(12) United States Patent
Connelly et al.

(10) Patent No.: US 8,784,467 B2
(45) Date of Patent: Jul. 22, 2014

(54) NON-OCCLUSIVE DILATION DEVICES

(75) Inventors: Ryan Connelly, Topsfield, MA (US); Jennifer Egan, Burlington, MA (US); Venkatesh Ramaiah, Scottsdale, AZ (US); Robert McNutt, Mesa, AZ (US)

(73) Assignee: LeMaitre Vascular, Inc., Burlington, MA (US)

(*) Notice: Subject to any disclaimer, the term of this patent is extended or adjusted under 35 U.S.C. 154(b) by 172 days.

(21) Appl. No.: 12/780,350

(22) Filed: May 14, 2010

(65) Prior Publication Data
US 2011/0082490 A1    Apr. 7, 2011

Related U.S. Application Data

(60) Provisional application No. 61/178,733, filed on May 15, 2009.

(51) Int. Cl.
| | | |
|---|---|---|
| *A61F 2/06* | (2013.01) | |
| *A61M 29/02* | (2006.01) | |
| *A61F 2/95* | (2013.01) | |
| *A61F 2/966* | (2013.01) | |

(52) U.S. Cl.
CPC ............. *A61M 29/02* (2013.01); *A61F 2/966* (2013.01); *A61F 2/95* (2013.01)
USPC ....... 623/1.11; 623/1.13; 623/1.15; 623/1.23; 606/198

(58) Field of Classification Search
CPC ............. A61F 2/06; A61F 2/86; A61F 2/88; A61F 2/95; A61F 2/954
USPC ............... 606/191–200; 623/1.11, 1.12, 1.13, 623/1.23, 2.11, 23.72
See application file for complete search history.

(56) References Cited

U.S. PATENT DOCUMENTS

| | | |
|---|---|---|
| 3,517,128 A | 6/1970 | Hines |
| 4,650,466 A | 3/1987 | Luther |

(Continued)

FOREIGN PATENT DOCUMENTS

| | | |
|---|---|---|
| EP | 1 574 169 | 9/2005 |
| FR | 2 735 967 | 1/1997 |

(Continued)

OTHER PUBLICATIONS

Macha et al., "Pigtail Catheters Used for Percutaneous Fluid Drainage: Comparison of Performance Characteristics", Radiology, vol. 238, No. 3 (Mar. 2006).

(Continued)

*Primary Examiner* — Darwin Erezo
*Assistant Examiner* — Kendra Obu
(74) *Attorney, Agent, or Firm* — Greenberg Traurig, LLP; David J. Dykeman; Danielle T. Abramson

(57) ABSTRACT

Non-occlusive modeling catheters including a dilation device for expanding an endoprosthesis implanted in a vessel are disclosed. In an embodiment, a modeling catheter includes a device comprising a plurality of compliant wires braided in a double overlapping pattern and having a length spanning between a proximal end of the device and a distal end of the device, wherein the device is positioned in at least a portion of an endoprosthesis implanted in a vessel, wherein, when the device is in a relaxed state, a plurality of spaces are formed between the plurality of wires to allow fluid to move freely through the plurality of spaces, and wherein, when the device is in a dilated state, the plurality of wires are sufficiently designed to exert a radial force on the endoprosthesis while continually allowing the fluid to move freely through the plurality of spaces.

28 Claims, 29 Drawing Sheets

(56) References Cited

U.S. PATENT DOCUMENTS

| | | |
|---|---|---|
| 4,759,045 A | 7/1988 | Lasky |
| 4,813,062 A | 3/1989 | Gilpatrick |
| 4,921,484 A | 5/1990 | Hillstead |
| 4,953,193 A | 8/1990 | Robinson |
| 5,068,886 A | 11/1991 | Lavia |
| 5,180,368 A | 1/1993 | Garrison |
| 5,195,123 A | 3/1993 | Clement |
| 5,257,975 A | 11/1993 | Foshee |
| 5,260,985 A | 11/1993 | Mosby |
| 5,263,963 A | 11/1993 | Garrison et al. |
| 5,354,310 A | 10/1994 | Garnic et al. |
| 5,527,282 A | 6/1996 | Segal |
| 5,626,602 A | 5/1997 | Gianotti et al. |
| 5,702,128 A | 12/1997 | Maxim et al. |
| 5,725,549 A | 3/1998 | Lam |
| 5,792,156 A | 8/1998 | Perouse |
| 5,817,102 A | 10/1998 | Johnson et al. |
| 5,848,125 A | 12/1998 | Arnett |
| 5,855,565 A | 1/1999 | Bar-Cohen et al. |
| 5,897,567 A | 4/1999 | Ressemann et al. |
| 5,916,235 A | 6/1999 | Guglielmi |
| 5,954,742 A | 9/1999 | Osypka |
| 6,096,053 A * | 8/2000 | Bates ............................ 606/159 |
| 6,206,868 B1 | 3/2001 | Parodi |
| 6,217,585 B1 | 4/2001 | Houser et al. |
| 6,263,236 B1 | 7/2001 | Kasinkas et al. |
| 6,312,407 B1 | 11/2001 | Zadno-Azizi et al. |
| 6,364,893 B1 | 4/2002 | Sahatjian et al. |
| 6,375,670 B1 | 4/2002 | Greenhalgh |
| 6,497,722 B1 | 12/2002 | Von Oepen et al. |
| 6,602,271 B2 | 8/2003 | Adams et al. |
| 6,632,236 B2 | 10/2003 | Hogendijk |
| 6,635,068 B1 | 10/2003 | Dubrul et al. |
| 6,673,042 B1 | 1/2004 | Samson et al. |
| 6,714,628 B2 | 3/2004 | Broyles et al. |
| 6,805,676 B2 | 10/2004 | Klint |
| 6,843,798 B2 | 1/2005 | Kusleika et al. |
| 6,913,618 B2 | 7/2005 | Denardo et al. |
| 6,928,146 B2 | 8/2005 | Broyles et al. |
| 7,087,062 B2 | 8/2006 | Dhindsa |
| 7,150,756 B2 | 12/2006 | Levinson et al. |
| 7,229,461 B2 | 6/2007 | Chin et al. |
| 7,232,453 B2 | 6/2007 | Shimon |
| 7,311,727 B2 | 12/2007 | Mazumder et al. |
| 7,331,975 B2 | 2/2008 | Yanuma et al. |
| 7,776,062 B2 | 8/2010 | Besselink et al. |
| 2002/0045916 A1 | 4/2002 | Gray et al. |
| 2003/0081732 A1 | 5/2003 | Broyles et al. |
| 2003/0083623 A1* | 5/2003 | Berg et al. ............... 604/164.13 |
| 2003/0139764 A1 | 7/2003 | Levinson et al. |
| 2003/0191521 A1 | 10/2003 | Denardo et al. |
| 2004/0015224 A1 | 1/2004 | Armstrong et al. |
| 2004/0044396 A1 | 3/2004 | Clerc et al. |
| 2004/0076261 A1 | 4/2004 | Broyles et al. |
| 2004/0199243 A1 | 10/2004 | Yodfat |
| 2004/0225346 A1 | 11/2004 | Mazumder et al. |
| 2004/0236351 A1 | 11/2004 | Yanuma et al. |
| 2004/0267355 A1 | 12/2004 | Scott et al. |
| 2006/0201601 A1 | 9/2006 | Furst et al. |
| 2006/0229645 A1 | 10/2006 | Bonnette et al. |
| 2007/0016243 A1 | 1/2007 | Ramaiah et al. |
| 2007/0299424 A1* | 12/2007 | Cumming et al. ............ 604/527 |
| 2008/0015633 A1* | 1/2008 | Abbott et al. ................ 606/207 |
| 2008/0058856 A1 | 3/2008 | Ramaiah et al. |
| 2008/0114439 A1 | 5/2008 | Ramaiah et al. |

FOREIGN PATENT DOCUMENTS

| | | |
|---|---|---|
| WO | WO 91/01773 | 2/1991 |
| WO | WO 96/01096 | 1/1996 |
| WO | WO 96/17645 | 6/1996 |
| WO | WO 97/14375 | 4/1997 |
| WO | WO 97/46174 | 12/1997 |
| WO | WO 99/47076 | 9/1999 |
| WO | WO 99/62430 | 12/1999 |
| WO | WO 01/37921 | 5/2001 |
| WO | WO 01/82831 | 11/2001 |
| WO | WO 2006/038873 | 4/2006 |
| WO | WO 2006/041607 | 4/2006 |
| WO | WO 2007/002863 | 1/2007 |
| WO | WO 2007/028112 | 3/2007 |
| WO | WO 2007/089897 | 8/2007 |
| WO | WO 2008/005405 | 1/2008 |
| WO | WO 2008/156468 | 12/2008 |

OTHER PUBLICATIONS

PCT International Search Report based on PCT/US2006/025458 dated Nov. 30, 2006.
PCT International Search Report based on PCT/US2007/015303 dated Apr. 28, 2008.
PCT International Search Report based on PCT/US2007/023087 dated Jul. 10, 2008.
Office Action in U.S. Appl. No. 11/478,340 mailed Apr. 2, 2009.
Office Action in U.S. Appl. No. 11/820,726 mailed Feb. 3, 2011.
European Search Report for European Patent Application No. 07853063.1 mailed Jun. 6, 2012.
Office Action in U.S. Appl. No. 11/977,415 mailed Mar. 22, 2011.
Office Action in U.S. Appl. No. 11/977,415 mailed Jul. 21, 2011.
Office Action in U.S. Appl. No. 11/977,415 mailed May 20, 2013.
Office Action in U.S. Appl. No. 11/977,415 mailed Mar. 12, 2014.

* cited by examiner

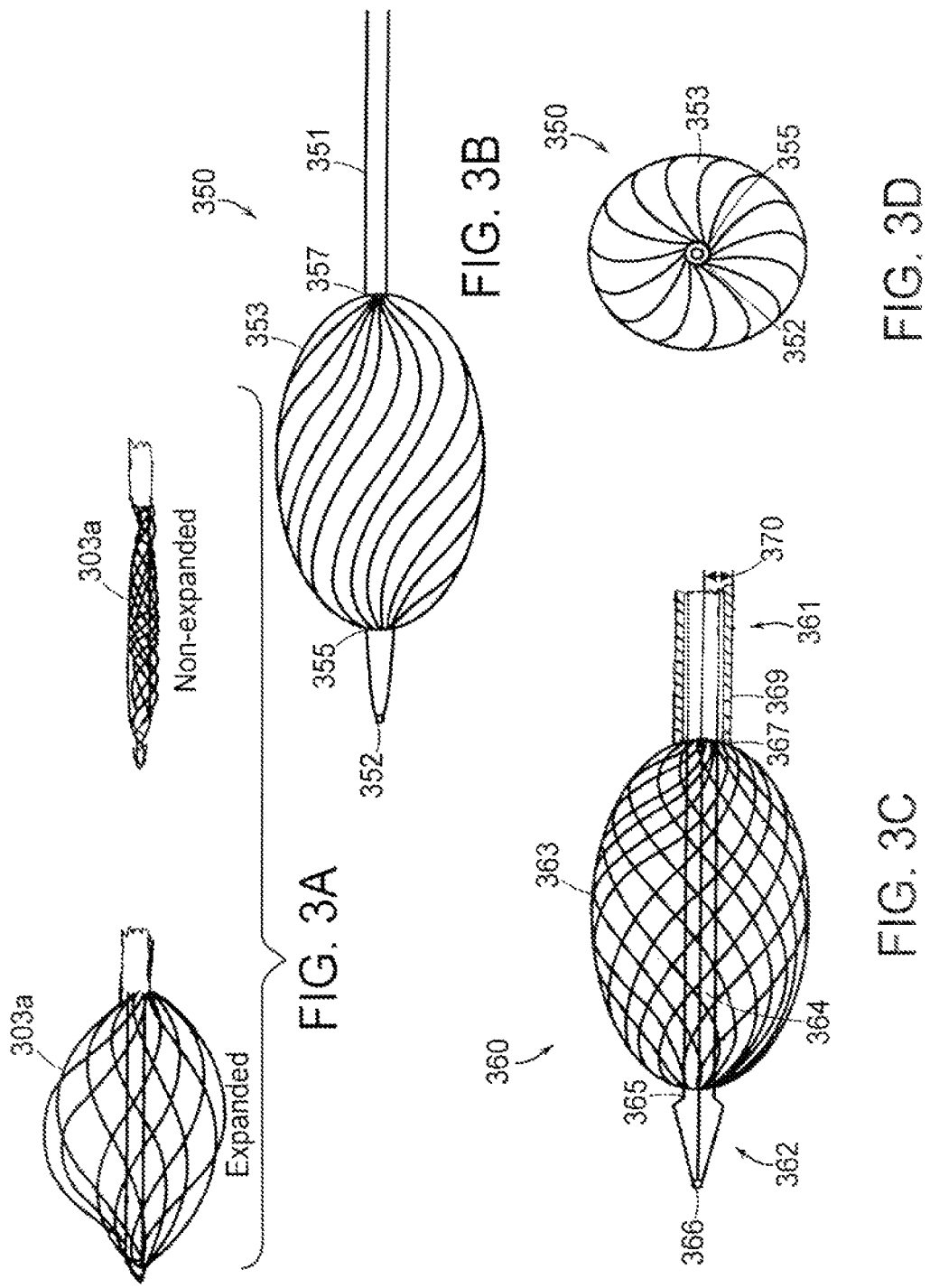

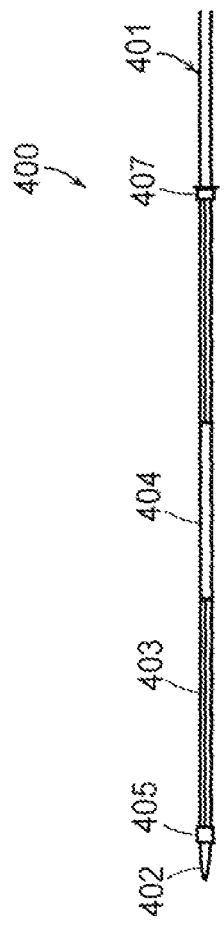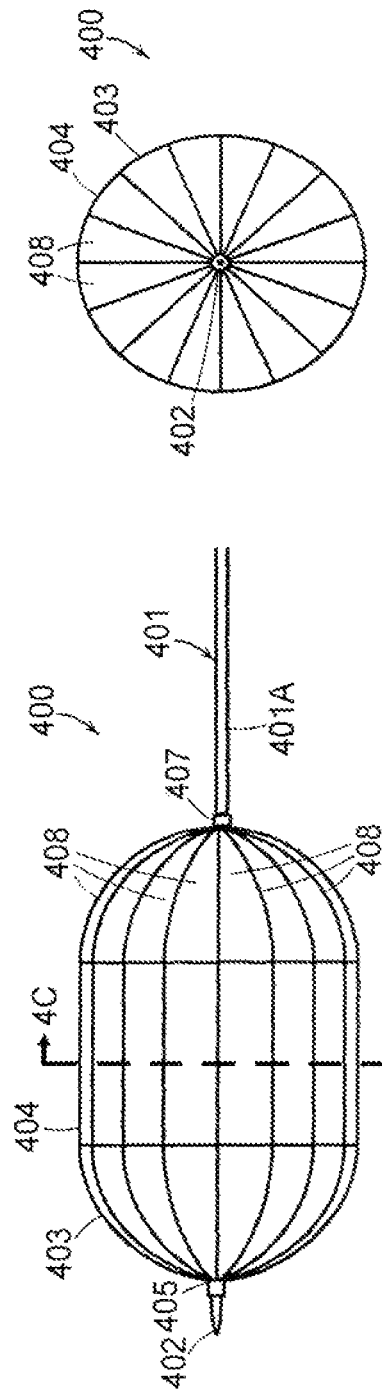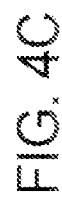

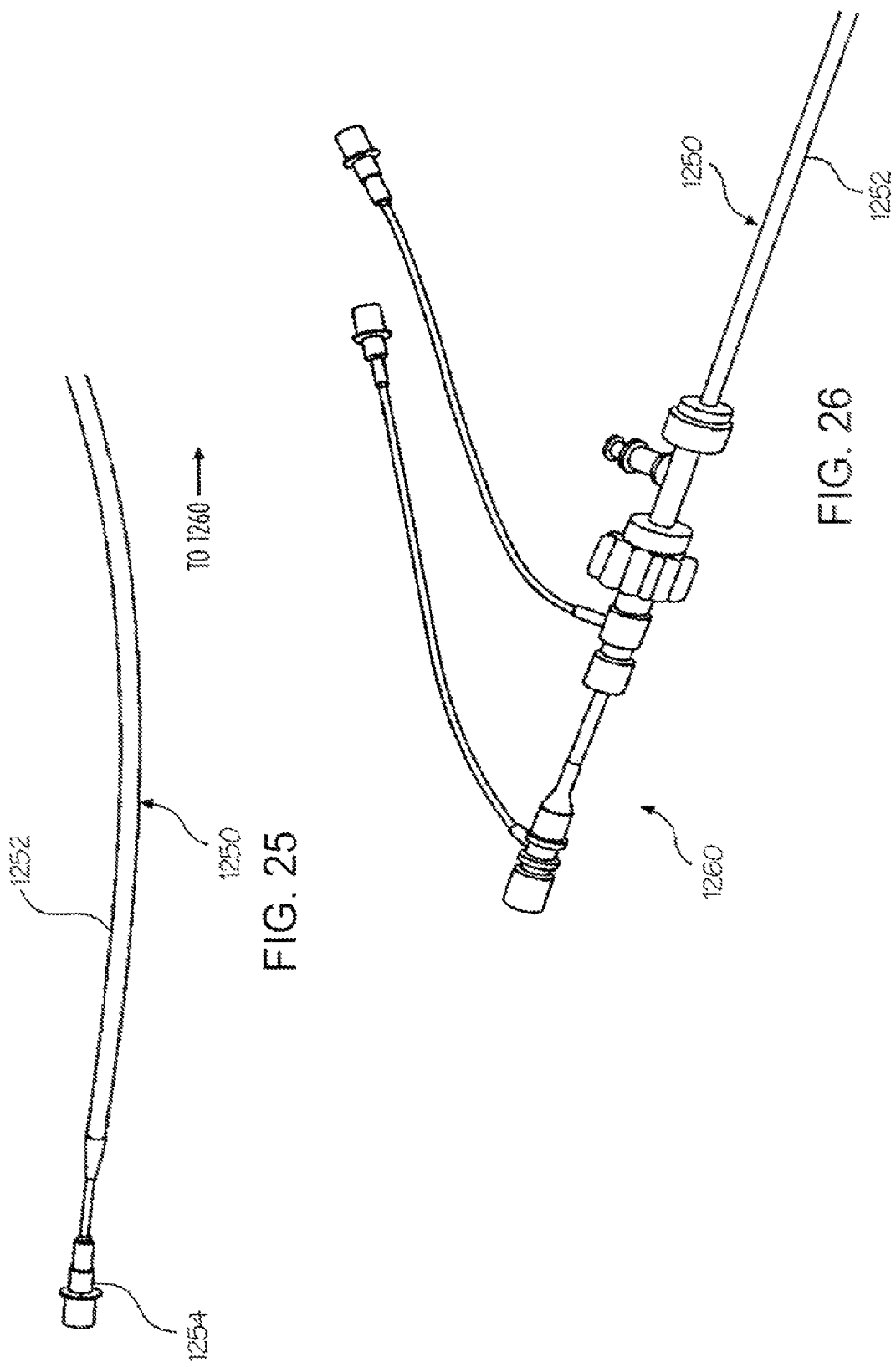

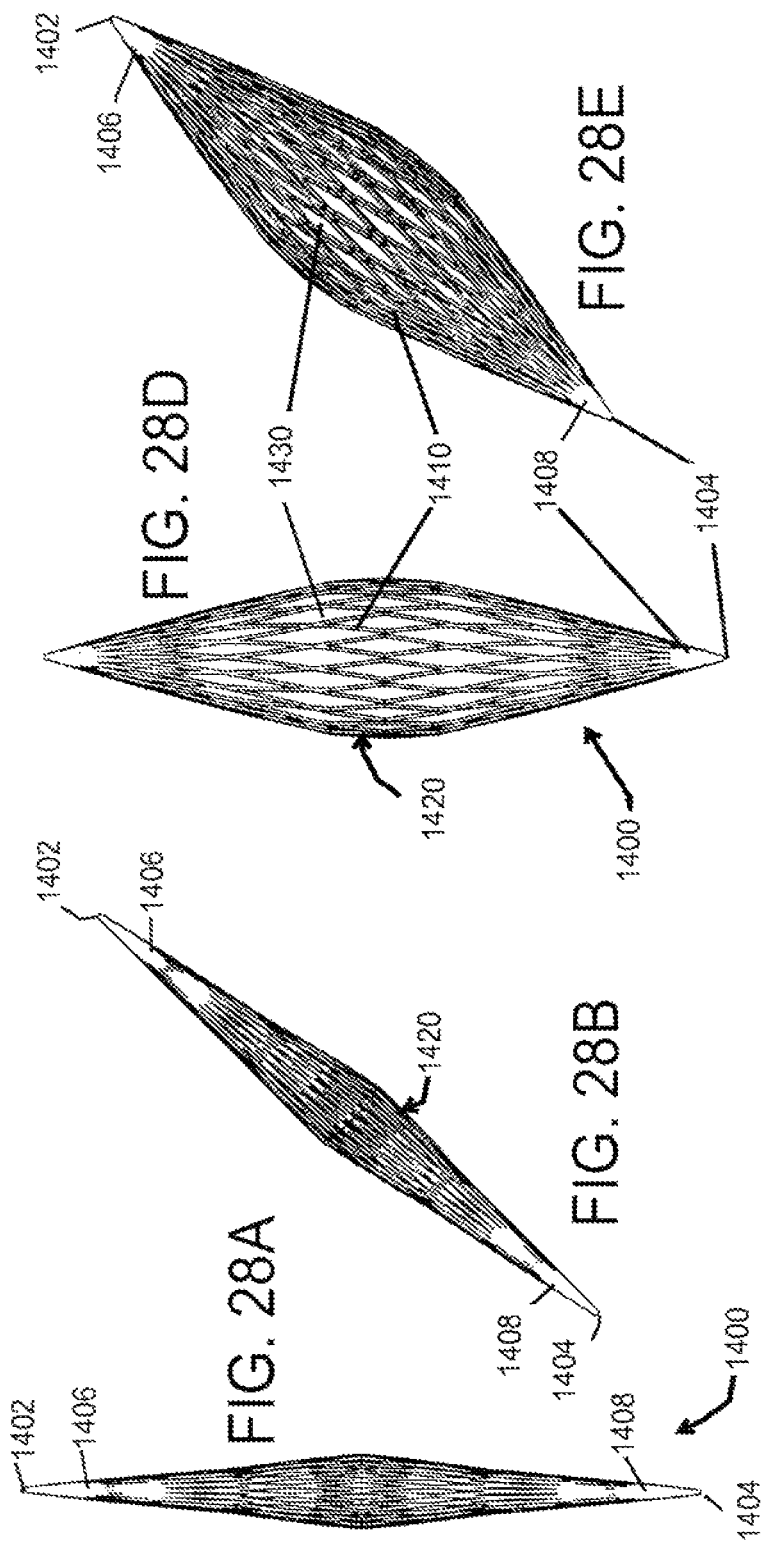

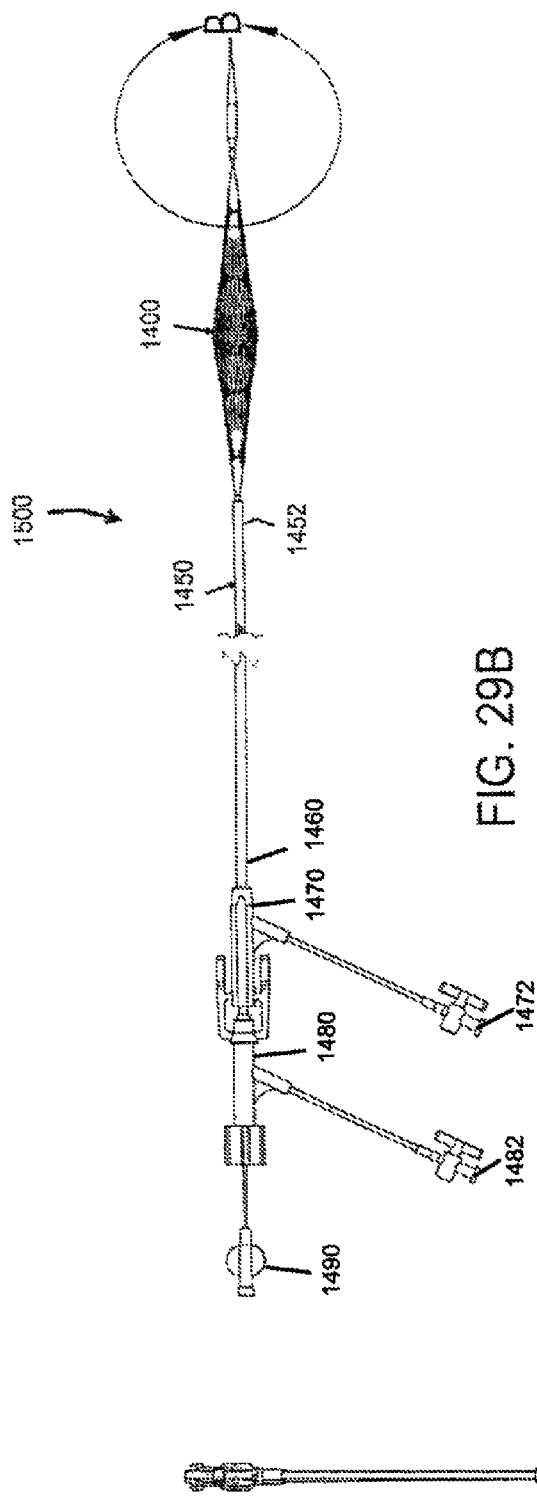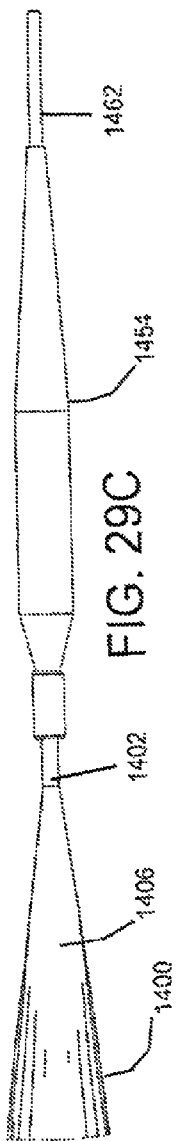
FIG. 29A
FIG. 29B
FIG. 29C

NON-OCCLUSIVE DILATION DEVICES

RELATED APPLICATIONS

This application claims the benefit of and priority to U.S. Provisional Application Ser. No. 61/178,733, filed May 15, 2009, the entirety of this application is hereby incorporated herein by reference.

FIELD

The embodiments disclosed herein relate to medical devices, and more particularly to non-occlusive modeling catheters for the dilation of blood vessels and/or the dilation of structures positioned within blood vessels.

BACKGROUND

Conventional systems for dilating blood vessels and/or structures (e.g., stents or stent grafts) positioned in a blood vessel utilize balloon-like structures ("balloon dilators"). Such structures are typically made from essentially impermeable materials. When such a device is expanded to perform a dilation, blood flow is entirely or substantially occluded through the blood vessel in which the balloon dilator is being used. Such an occlusion of blood flow could, if continued for too long, harm the patient, since portions of the body downstream of the balloon dilator will not receive blood while the flow is occluded or substantially hindered. Thus, the length of time balloon dilators may be dilated is limited and this can hinder proper completion of the dilation procedure.

A similar problem with balloon dilators arises when a dilation procedure is being performed in a portion of the circulatory system where there is a branch in the blood vessels, such as where the iliac or renal arteries are side vessels that branch from the aorta. In that case a balloon dilator may cover a side vessel and partially or totally occlude blood flow to the side vessel.

Another problem with balloon-like dilators is called the "jackhammer effect." Because blood flow is substantially or entirely occluded when balloon dilators are dilated, the blood pressure upstream of the balloon dilator can be significant and may cause the balloon dilator, and any structure (such as a stent or stent graft) positioned in the blood vessel and that is being dilated by the balloon dilator, to move out of the desired position, effectively pushed down stream (i.e., in the antegrade direction) by the upstream blood pressure. Because of this problem accurate placement of such structures can be difficult utilizing balloon dilators.

SUMMARY

The embodiments disclosed herein relate to medical devices, and more particularly to non-occlusive modeling catheters for the dilation of blood vessels and/or the dilation of structures positioned within blood vessels. The non-occlusive modeling catheters of the present disclosure may be used in any medical application in which dilation of a vessel and/or dilation of a structure positioned within a vessel (e.g., a stent or stent graft, such as a thoracic or abdominal aortic stent graft) is desired. In an embodiment, a non-occlusive modeling catheter of the present disclosure includes a triaxial catheter and a dilation device. In an embodiment, a dilation device of the present disclosure is used to enhance primary attachment of a structure positioned within a vessel. In an embodiment, a dilation device of the present disclosure is used to repair a collapse of a structure positioned within a vessel. In an embodiment, a dilation device of the present disclosure is used to repair infolding of a structure positioned within a vessel. In an embodiment, a dilation device of the present disclosure is used to repair an endoleak in a structure positioned within a vessel, while minimizing the risk of endoprosthesis migration. A dilation device of the present disclosure is sufficiently designed so that when the dilation device is positioned within a structure implanted within a vessel, and the dilation device is unsheathed, the dilation device does not occlude or substantially hinder the flow of fluid through the structure. A dilation device of the present disclosure is sufficiently designed so that when the dilation device is positioned within a vessel, and the dilation device is unsheathed, the dilation device does not occlude or substantially hinder the flow of fluid through the vessel or through side vessels that are connected to the vessel. In an embodiment, a dilation device of the present disclosure includes a plurality of wires and has at least a first position in which the dilation device is collapsed and can be moved into or retrieved from a vessel or structure within a vessel, at least a second position in which the dilation device is in a relaxed state, and at least a third position in which the dilation device is dilated and dilates the vessel or a structure within the vessel. When in a relaxed state or a dilated state, fluid is capable of passing through the plurality of wires of the dilation device by virtue of a plurality of openings or spaces created between the plurality of wires.

According to aspects illustrated herein, there is disclosed a dilation device that includes a wire mesh that may be spiraled, formed in a criss-cross pattern or formed in any suitable pattern. The expansion and contraction of the dilation device may be accomplished using a twisting motion (especially for a dilation device having a spiraled wire mesh pattern) or by applying linear pressure to the dilation device such as through a pushing or pulling motion by an operator, which compresses the dilation device along the axis of a catheter to which the dilation device is attached and causes the dilation device to dilate. The dilation device can be contracted and collapsed by reversing the twisting motion or by releasing the linear pressure.

According to aspects illustrated herein, there is disclosed a dilation device that includes a plurality of wires that are substantially parallel to the vessel flow path when inserted in a vessel. The expansion and contraction of such a dilation device may be accomplished by applying linear pressure to the dilation device such as through a pushing or pulling motion by an operator to compress the dilation device and expand the dilation device, and by releasing the linear pressure to contract and collapse the dilation device.

Any dilation device according to the present disclosure may be preshaped so that the dilation device automatically expands into a set or relaxed position when released from a catheter sheath. The dilation device can then be dilated further or contracted by an operator in one of the manners described herein. An additional advantage of this particular design is that the dilation device takes less time and operator effort to dilate or contract the dilation device to the proper dimension for use in a procedure since the dilation device is preshaped to expand to a diameter (relaxed diameter) close to the desired diameter (dilated diameter).

Any dilation device according to the present disclosure is preferably mounted on a catheter and, utilizing the catheter, the dilation device is positioned at the proper place within a vessel and then dilated. The catheter may be biaxial (without a cover sheath) or triaxial (with a cover sheath).

According to aspects illustrated herein, there is disclosed a dilation device for dilating either a vessel or a structure positioned within the vessel that includes a proximal end, a distal end, and a body portion comprising a plurality of wires, wherein the dilation device has a length from the proximal end to the distal end of between about 7 and about 15 centimeters. In an embodiment, the dilation device has 48 wires. In an embodiment, the wires have a diameter of about 0.011 inches. The dilation device is sufficiently designed to move from a relaxed, collapsed position to a partially or fully dilated, expanded position. In an embodiment, the dilation device has a collapsed diameter of about 4 millimeters. In an embodiment, the dilation device has a relaxed diameter of about 25 millimeters. In an embodiment, the dilation device has a fully dilated diameter of about 55 millimeters. When the dilation device is in the relaxed position, or moved to a partially of fully dilated position, spaces exist between the plurality of wires. In an embodiment, these spaces range from about 0.5 mm$^2$ to about 5 mm$^2$. In an embodiment, the dilation device has a kink radius of about 50.8 mm. In an embodiment, the dilation device is used to dilate a single vessel having a variable diameter along a length of the vessel. In such embodiments, the dilation device is able to conform to a diameter disparity ratio up to about 13.13:1. In an embodiment, the dilation device is used to dilate multiple vessels having different diameters. In such embodiments, the dilation device is able to conform to a multi-vessel diameter disparity ratio up to about 20:1. In an embodiment, when the dilation device is dilated within the vessel, a pressure drop in the vessel is about zero. In an embodiment, the dilation device exerts a radial pressure as the dilation device is dilated that ranges from about 0 to about 10.5 pounds per square inch. In an embodiment, the radial pressure is exerted over an entire working range of the dilation device.

According to aspects illustrated herein, there is disclosed a device that includes a plurality of compliant wires braided in a double overlapping pattern and having a length spanning between a proximal end of the device and a distal end of the device, wherein the device is positioned in at least a portion of an endoprosthesis implanted in a single vessel, wherein, when the device is in a relaxed state, a plurality of spaces are formed between the plurality of wires to allow fluid to move freely through the plurality of spaces, wherein, when the device is in a dilated state, the plurality of wires are sufficiently designed to exert a radial force on the endoprosthesis while continually allowing the fluid to move freely through the plurality of spaces, and wherein, when the device is in the dilated state, the plurality of wires are sufficiently designed to conform to a diameter disparity ratio in the single vessel ranging from about 1:1 to about 10:1. In an embodiment, the device is positioned in the endoprosthesis to enhance primary attachment of the endoprosthesis to the single vessel. In an embodiment, the device is positioned in the endoprosthesis to repair a collapse in the endoprosthesis. In an embodiment, the device is positioned in the endoprosthesis to repair infolding of the endoprosthesis. In an embodiment, the device is positioned in the endoprosthesis to repair an endoleak in the endoprosthesis.

According to aspects illustrated herein, there is disclosed a device that includes a plurality of compliant wires braided in a double overlapping pattern and having a length spanning between a proximal end of the device and a distal end of the device, wherein the device is sufficiently designed to expand from a relaxed state to a dilated state, wherein the device is positioned in at least a portion of an endoprosthesis implanted in a bifurcated vessel, wherein, when the device is in the relaxed state, the overlapping pattern creates a plurality of spaces between the plurality of wires allowing fluid to move freely through the plurality of spaces, wherein, when the device is in the dilated state, the plurality of wires are sufficiently designed to exert a radial force on the endoprosthesis while continually allowing the fluid to move freely through the plurality of spaces, and wherein, when the device is in the dilated state, the plurality of wires are sufficiently designed to conform to a multi-vessel diameter disparity ratio in the bifurcated vessel ranging from about 2:1 to 20:1. In an embodiment, the device is positioned in the endoprosthesis to enhance primary attachment of the endoprosthesis to the single vessel. In an embodiment, the device is positioned in the endoprosthesis to repair a collapse in the endoprosthesis. In an embodiment, the device is positioned in the endoprosthesis to repair infolding of the endoprosthesis. In an embodiment, the device is positioned in the endoprosthesis to repair an endoleak in the endoprosthesis.

According to aspects illustrated herein, there is disclosed a modeling catheter that includes a device comprising a plurality of compliant wires braided in an overlapping pattern and having a length spanning between a proximal end of the device and a distal end of the device, wherein a plurality of spaces are formed between the plurality of compliant wires to allow fluid to move freely through the plurality of spaces; a central tube having a proximal portion, a distal portion, and a central portion passing through the device; an outer tube positioned coaxially around the proximal portion of the central tube and engaging the proximal end of the device; a proximal retention end engaging the outer tube at a first end and engaging the proximal end of the device at a second end; a distal retention end engaging the central tube at a first end and engaging the distal end of the device at a second end; and a retractable sheath positioned coaxially around the outer tube and slidably moveable over the device to selectively collapse the device, relax the device, and dilate the device.

According to aspects illustrated herein, there is disclosed a method of modeling an endoprosthesis that includes gaining access to an endoprosthesis positioned in a vessel; guiding a dilation device of the present disclosure into position within the endoprosthesis using a guide wire so that an intended modeling zone is between two radio-opaque marker bands located on the dilation device, wherein the dilation device is fully sheathed during positioning; unsheathing the dilation device in the endoprosthesis; expanding the dilation device to model the endoprosthesis to a wall of the vessel, wherein the dilation device is expanded until a desired amount of radial force is exerted on the endoprosthesis; collapsing the dilation device; resheathing the dilation device fully; and removing the dilation device from the endoprosthesis. In an embodiment, the expansion and the collapsing of the dilation device is repeated as necessary to model the endoprosthesis to the wall of the vessel. In an embodiment, the method further includes confirming that the endoprosthesis has not moved in the vessel. In an embodiment, the endoprosthesis is positioned in a single vessel. In an embodiment, the single vessel has a straight length. In an embodiment, the single vessel has a bend. In an embodiment, the single vessel has a diameter disparity ratio in the modeling zone. In an embodiment, the endoprosthesis is positioned in a bifurcated vessel. In an embodiment, the bifurcated vessel has a multi-vessel diameter disparity ratio in the modeling zone.

Various embodiments provide certain advantages. Not all embodiments of the invention share the same advantages and those that do may not share them under all circumstances. Further features and advantages of the embodiments, as well as the structure of various embodiments are described in detail below with reference to the accompanying drawings.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 3A shows an embodiment of a dilation device in an expanded position and in a non-expanded position;

FIG. 3B shows a partial, side view of an embodiment of a dilation device in an expanded position and a catheter of the present disclosure;

FIG. 3C shows a partial, sectional side view of an embodiment of a dilation device and a catheter of the present disclosure;

FIG. 3D shows a front view of the dilation device of FIG. 3B;

FIG. 4A shows a partial, side view of an embodiment of a dilation device in a first position and a catheter of the present disclosure;

FIG. 4B shows a partial, side view of the dilation device of FIG. 4A in an expanded position;

FIG. 4C shows a sectional view taken along line 4C-4C of FIG. 4B of the dilation device of FIG. 4B;

FIG. 25 is a perspective view of a distal end of the dilation device of FIG. 13 with the dilation device enclosed within an outer sheath of the catheter;

FIG. 26 is a perspective view of a proximal end of the catheter of FIG. 13;

FIG. 28A shows a side view of an embodiment of a dilation device of the present disclosure;

FIG. 28B shows a perspective side view of the dilation device of FIG. 28A;

FIG. 28C shows an end view of the dilation device of FIG. 28A;

FIG. 28D shows a side view of the dilation device of FIG. 28A in a partially dilated position;

FIG. 28E shows a perspective, side view of the dilation device of FIG. 28A in a partially dilated position;

FIG. 28F shows an end view of the dilation device of FIG. 28A in a partially dilated position;

FIG. 29A shows a view of an embodiment of a modeling catheter of the present disclosure including a dilation device;

FIG. 29B shows a side view of the modeling catheter of FIG. 29A;

FIG. 29C shows an enlarged view of the encircled region B of FIG. 29B;

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

As used herein, the term "assembly" refers to a dilation device according to embodiments of the present disclosure assembled as part of or connected to a catheter so that it can be advanced into a vessel.

Figure 22:
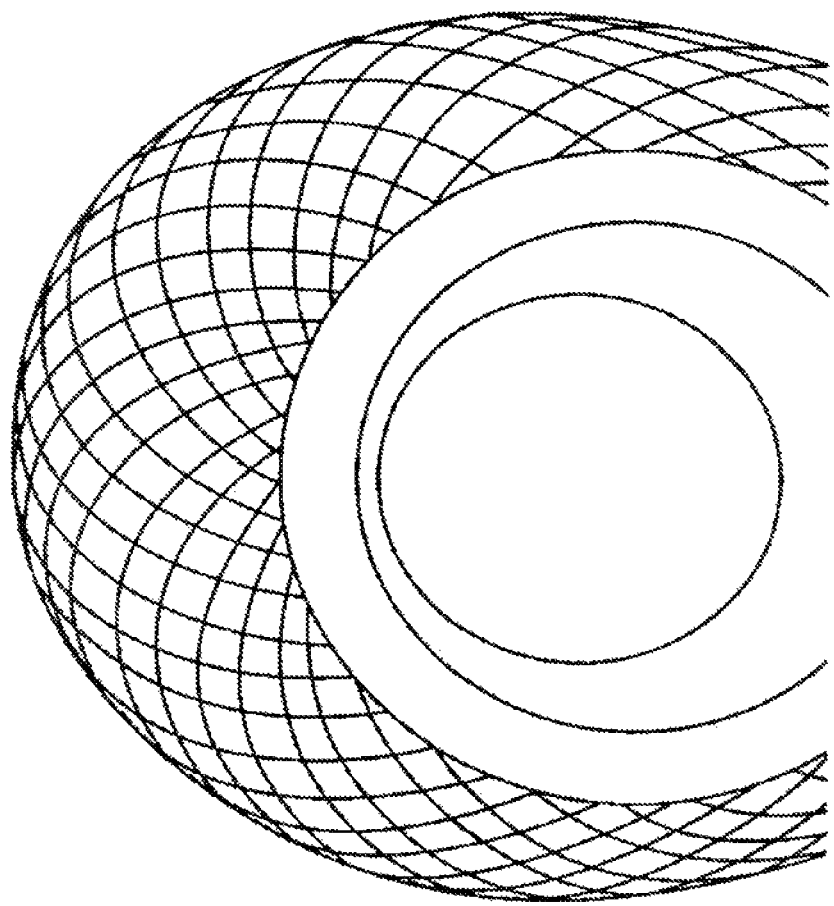
FIG. 22 shows a bend radius of a dilation device of the present disclosure in a partially dilated position.
Figure 21:
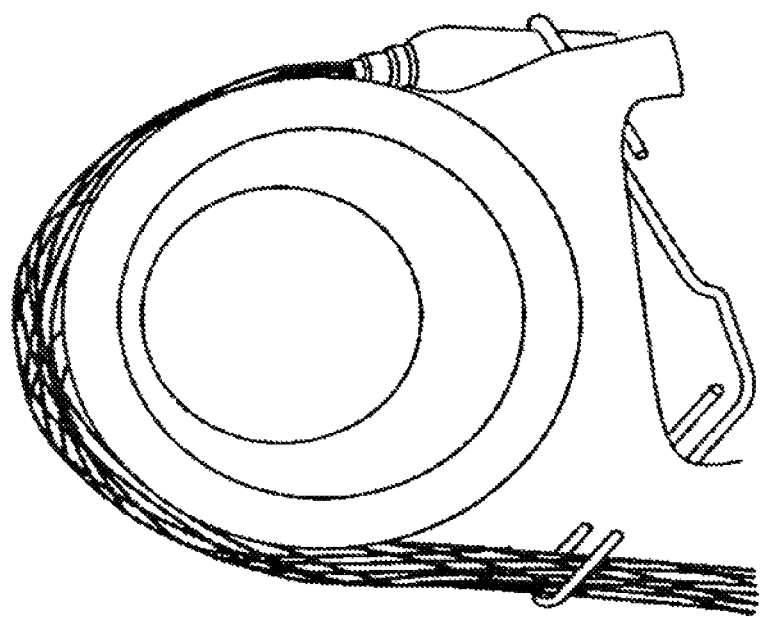
FIG. 21 shows a bend radius of a dilation device of the present disclosure in a collapsed position.
Figure 23:
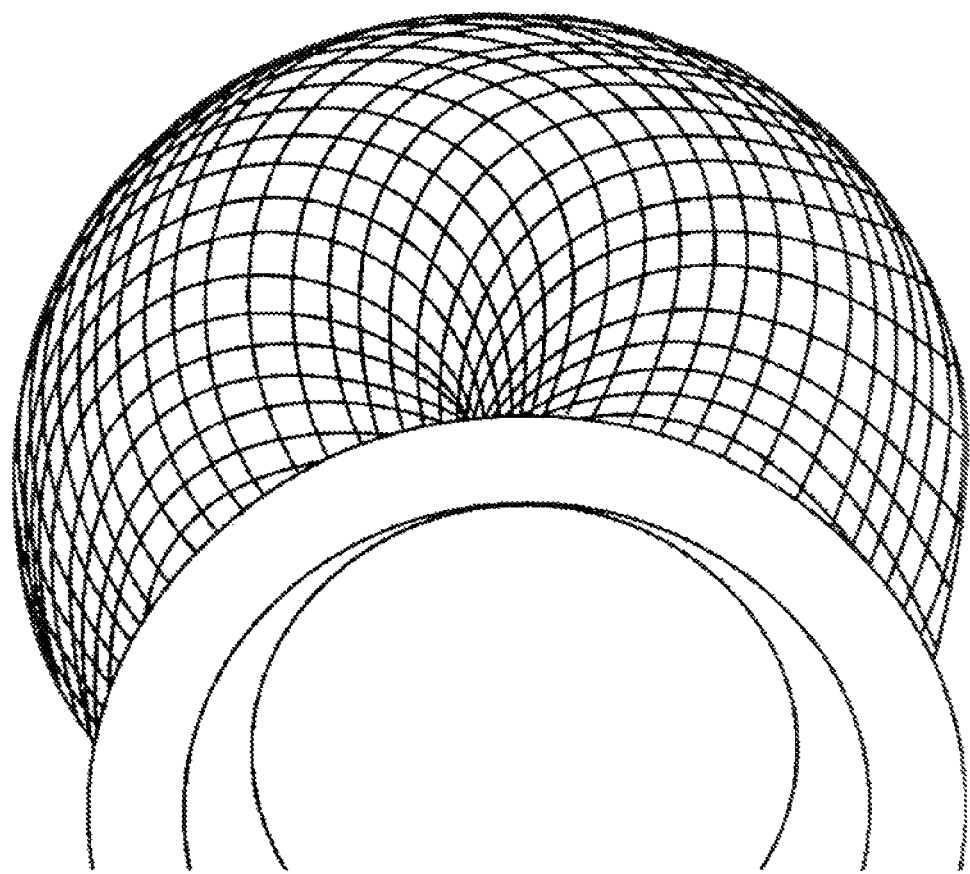
FIG. 23 shows a bend radius of a dilation device of the present disclosure in a fully dilated position.

As used herein, the term "bend radius" refers to the minimum radius to which a dilation device according to the present disclosure can be deformed or bent in use without the wires of the dilation device being damaged (i.e., without "kinking"). If the dilation device is mounted on a catheter the bend radius refers to the bend radius of the entire assembly, i.e., the dilation device mounted to a biaxial or triaxial catheter (with the sheath covering the device), since the entire assembly moves through the vessel when the device is advanced into place. The smaller the bend radius, the greater the resistance of the device or assembly to kinking FIGS. 21-23 show measurement of the bend radius with respect to an embodiment of the present disclosure.

As used herein, the term "bifurcation" refers to a division point from one unit into two or more units. Generally, bifurcations of a body lumen are defined as 1) a continuous main lumen having at least one branch lumen that extends or branches off from the main lumen, or 2) a first lumen (also referred to as a parent lumen) that splits into at least first and second branch lumens. The term lumen means the cavity of a tubular structure. An example bifurcation is a vessel bifurcation that includes a continuous main vessel and a branch vessel that branches off from the main vessel. A vessel bifurcation can alternatively include a parent vessel that divides into first and second branch vessels. In an embodiment, a dilation device of the present disclosure is used at a vessel bifurcation, such as the aortic bifurcation. The aortic bifurcation is the point at which the abdominal aorta bifurcates into the left and right common iliac arteries.

As used herein, the term "collapsed" refers to a dilation device in a position other than a relaxed position or dilated position. A dilation device of the present disclosure would normally be in a collapsed position when introduced into a vessel and/or when retained within a cover sheath of a triaxial catheter.

As used herein, the term "contraction" of a dilation device or "contracting" a dilation device refers to a diameter of the dilation device is being or has been reduced from a less contracted or dilated position.

As used herein, the term "criss-cross" pattern refers to a wire pattern wherein the wires cross one another as shown, for example, in the embodiments depicted in FIGS. 13-20.

As used herein, the term "device" or "dilation device" refers to a structure for (a) dilating one or more vessels, and/or (b) dilating a structure inside of one or more vessels (such as an endograft stent or stent graft) to be deployed or repositioned within one or more vessels.

As used herein, the term "diameter" as used in connection with a vessel refers to the approximate diameter of a vessel since vessels are not often perfectly cylindrical. "Diameter" as used with respect to any structure means an approximate diameter.

As used herein, the term "diameter disparity ratio" refers to the disparity between multiple diameters of a single vessel. Vessels, particularly diseased vessels, may not have a relatively constant diameter and the diameter can suddenly increase (due to, for example, an aneurysm) or decrease (due to, for example, contraction of the muscular wall of the vessel). For example, the diameter of a vessel may suddenly change from an initial diameter to a diameter of 1.5 times the initial diameter, in which case the diameter disparity ratio would be 1.5:1. A diameter disparity ratio to which a dilation device according to some aspects of the present disclosure could conform is one or more of the ratios between about 1.1:1 and about 20:1, including diameter disparity ratios of approximately 1.2:1, 1.4:1, 1.6:1, 1.8:1, 2.0:1, 2.2:1, 2.4:1, 2.6:1, 2.8:1, 3.0:1, 3.4:1, 3.6:1, 3.8:1, 4.0:1, 4.2:1, 4.4:1, 4.6:1, 4.8:1, 5.0:1, 5.2:1, 5.4:1, 5.6:1, 5.8:1, 6.0:1, 6.2:1, 6.4:1, 6.6:1, 6.8:1, 7.0:1, 7.2:1, 7.4:1, 7.6:1, 7.8:1, 8.0:1, 8.2:1, 8.4:1, 8.6:1, 8.8:1, 9.0:1, 9.2:1, 9.4:1, 9.6:1, 9.8:1, 10.0:1, 10.2:1, 10.4:1, 10.6:1, 10.8:1, 11.0:1, 11.2:1, 11.4:1, 11.6:1, 11.8:1, 12.0:1, 12.2:1, 12.4:1, 12.6:1, 12.8:1, 13.0:1, 13.2:1, 13.4:1, 13.6:1, 13.8:1, 14.0:1, 14.2:1, 14.4:1, 14.6:1, 14.8:1, 15.0:1, 15.2:1, 15.4:1, 15.6:1, 15.8:1, 16.0:1, 16.2:1, 16.4:1, 16.6:1, 16.8:1, 17.0:1, 17.2:1, 17.4:1, 17.6:1, 17.8:1, 18.0:1, 18.2:1, 18.4:1, 18.6:1, 18.8:1, 19.0:1, 19.2:1, 19.4:1, 19.6:1, 19.8:1, 20.0:1, and including diameter disparity rations of greater than 20.0:1 and less than 1.2:1.

As used herein, the term "dilated" means a dilation device in an expanded position. A dilation device dilated within a vessel may be dilated for the purpose of dilating the vessel itself and/or for dilating a structure within the vessel. "Expanded" and "dilated" may be used interchangeably when used in connection with a dilation device.

As used herein, the term "endoprosthesis" means a tubular member that is placed in a body, for example, in a lumen (such as a blood vessel) in a body. Examples of endoprostheses include, but are not limited to, stents, covered stents, and stent-grafts.

As used herein, the term "fluid" means any substance, such as a liquid or gas, that can flow, including bodily fluids, such as blood and blood plasma, amniotic fluid, aqueous humour, cerumen (also known as earwax), ejaculates, chyme, interstitial fluid, lymph, breast milk, mucus (including nasal drainage and phlegm), pleural fluid, pus, saliva, sebum (skin oil), semen, serum, sweat, tears, urine, vaginal secretions and vomit.

As used herein, the term "fully dilated" or "fully expanded" means the maximum amount a dilation device can be dilated (as measured at its greatest diameter) when unhindered by external structures (such as a vessel) and when dilated using the delivery system of a catheter to which the dilation device engages.

As used herein, the term "kink radius" refers to the radius (diameter) of curvature which can be imposed on a dilation device according to the present disclosure that results in the kinking of the dilation device. It should be appreciated that the kink radius of a dilation device may be tested in a collapsed state, a relaxed state, and an expanded or dilated state. The fact that a dilation device can achieve such kink radii may be important for use of the device in a vessel having a bend, such as the aorta, as well as the ability of the device to model endoprostheses having curved configurations. In an embodiment, a dilation device of the present disclosure is sufficiently designed to have a kink radius configured to provide sufficient radial force at, for example, a bend in a vessel. In an embodiment, the radial force is substantially equal along a working length of the dilation device. In an embodiment, the dilation device is sufficiently designed so that at a dilation device having any desired length will produce a substantially equal radial force at a bend in the vessel at both an inner curvature of the vessel and the outer curvature of the vessel.

As used herein, the term "modeling" means expanding all or a portion of an endoprosthesis using a non-occlusive dilation device of the present disclosure. In an embodiment, modeling is performed to enhance primary attachment of an endoprosthesis to a single vessel. In an embodiment, modeling is performed to repair a collapse in an endoprosthesis. In an embodiment, modeling is performed to repair infolding of an endoprosthesis. In an embodiment, modeling is performed to repair an endoleak in an endoprosthesis. "Modeling zone" means that area of an endoprosthesis where modeling is required. In an embodiment, a non-occlusive dilation device of the present disclosure is positioned so that the intended modeling zone is between two radio-opaque marker bands located on the dilation device.

As used herein, the term "multi-vessel diameter disparity ratio" means the disparity of the diameters of two or more vessels. A dilation device may be deployed and dilated within two vessels simultaneously and the two vessels may have different, respective diameters. For example, if one vessel has a first diameter and the second vessel has a second diameter 1.8 times as large as the first diameter, the multi-vessel diameter disparity ratio would be 1.8:1. For example, if one vessel has an aneurysm with a first diameter In some embodiments, a dilation device could conform to one or more of the multi-vessel diameter disparity ratios between 1:1 and 10:1. In an embodiment, a dilation device of the present disclosure is used for treatment of bifurcated lumens in a patient, such as a vessel bifurcation. In an embodiment, a dilation device of the present disclosure is sufficiently designed to have a multi-vessel diameter disparity ratio of about 5:1 to conform to a vessel bifurcation. A multi-vessel diameter disparity ratio to which a dilation device according to some aspects of the present disclosure could conform is one or more of the ratios between about 1.1:1 and about 20:1, including multi-vessel diameter disparity ratios of approximately 1.2:1, 1.4:1, 1.6:1, 1.8:1, 2.0:1, 2.2:1, 2.4:1, 2.6:1, 2.8:1, 3.0:1, 3.4:1, 3.6:1, 3.8:1, 4.0:1, 4.2:1, 4.4:1, 4.6:1, 4.8:1, 5.0:1, 5.2:1, 5.4:1, 5.6:1, 5.8:1, 6.0:1, 6.2:1, 6.4:1, 6.6:1, 6.8:1, 7.0:1, 7.2:1, 7.4:1, 7.6:1, 7.8:1, 8.0:1, 8.2:1, 8.4:1, 8.6:1, 8.8:1, 9.0:1, 9.2:1, 9.4:1, 9.6:1, 9.8:1, 10.0:1, 10.2:1, 10.4:1, 10.6:1, 10.8:1, 11.0:1, 11.2:1, 11.4:1, 11.6:1, 11.8:1, 12.0:1, 12.2:1, 12.4:1, 12.6:1, 12.8:1, 13.0:1, 13.2:1, 13.4:1, 13.6:1, 13.8:1, 14.0:1, 14.2:1, 14.4:1, 14.6:1, 14.8:1, 15.0:1, 15.2:1, 15.4:1, 15.6:1, 15.8:1, 16.0:1, 16.2:1, 16.4:1, 16.6:1, 16.8:1, 17.0:1, 17.2:1, 17.4:1, 17.6:1, 17.8:1, 18.0:1, 18.2:1, 18.4:1, 18.6:1, 18.8:1, 19.0:1, 19.2:1, 19.4:1, 19.6:1, 19.8:1, 20.0:1, and including multi-vessel diameter disparity rations of greater than 20.0:1 and less than 1.2:1.

As used herein, the term "non-occlusive modeling assembly" means a catheter comprising a dilation device of the present disclosure for assisting in the modeling of an endoprosthesis, such as a stent graft. Expanding stent grafts may enhance the contact between the stent graft and a vessel wall, and eliminate fabric wrinkles In an embodiment, the dilation devices disclosed herein are fabricated from a nitinol material. In an embodiment, the non-occlusive modeling assemblies disclosed herein are intended to assist in the modeling of self expanding endoprostheses in large diameter vessels. Large diameter vessels may have diameters from about 15 mm to about 55 mm, such as the aorta and the pulmonary artery.

As used herein, the term "pressure drop" refers to the reduction in pressure in part of a vessel when a dilation device is (a) dilated within the vessel, or (b) dilated in another vessel but totally or partially covering the opening to the vessel (in which case the vessel may be referred to as a "side vessel"). When a balloon dilator is fully dilated within a vessel the pressure upstream of the balloon dilator increases significantly while the pressure downstream of the balloon dilator, or in a side vessel covered by the balloon dilator, can reach substantially zero (meaning that the balloon dilator has blocked most or all of the blood flow). As an example, if the pressure at a location in a vessel is 100 mm Hg (i.e., a pressure of 100 millimeters of mercury) before a device is dilated within the vessel, and the pressure at the same location in the vessel is 10 mmHG after the device is dilated, the pressure drop would be 90%, i.e., 100−10=90, and 90/100=90%. Similarly, for the same vessel if the pressure after dilation were 20 mmHg the pressure drop would be 80%, if the pressure after dilation were 30 mmHg the pressure drop would be 70%, if the pressure after dilation were 5 mmHg the pressure drop would be 95% and if the pressure after dilation were 1 mmHg the pressure drop would be 99%.

As used herein, the term "relaxed shape" or "relaxed state" means a natural shape of a dilation device of the present disclosure when no external forces or stresses are being applied to the dilation device. A dilation device of the present disclosure is compressed or collapsed when it is positioned in a cover sheath.

As used herein, the term "strut" means a wire having a generally rectangular (preferably with radiused edges) cross-section with generally flat top and bottom surfaces and having a width greater than its thickness.

As used herein, the term "vessel" means any vessel within a body, such as the human body, through which blood or other fluid flows and includes arteries and veins.

As used herein, the term "vessel flow path" means the direction of fluid flow through a vessel.

As used herein, the term "wire" means any type of wire, strand, strut or structure, regardless of cross-sectional dimension (e.g., the cross-section could be circular, oval, or rectangular) or shape, and regardless of material, that may be used to construct a dilation device as described herein. Some wires may be suitable for one or more of the embodiments but not suitable for others.

The dilation devices of the present disclosure find use in dilating a vessel and/or an endoprosthesis (such as an endograft, stent or stent graft) positioned in a vessel, or alternatively may be used to simultaneously dilate two vessels or dilate an endoprosthesis positioned in two vessels. In an embodiment, a dilation device of the present disclosure comprises a plurality of wires and is sufficiently designed to be placed in a first position wherein the dilation device is collapsed. In this first position, the dilation device has a sufficiently small enough diameter to be positioned in a vessel where the dilation device is to be used. The dilation device also has a second position, wherein the dilation device is relaxed. In this second position, the dilation no external forces or stresses are applied to the dilation device. The dilation device also has a third, fourth, and possible additional positions, wherein the dilation device is partially or fully dilated in order to dilate a vessel and/or a structure within the vessel. When relaxed and dilated, the wires of the dilation device are spaced apart to allow for the passage of fluid through the dilation device. Thus, the dilation device is designed so that the dilation device does not occlude or substantially hinder the flow of fluid through the vessel. The dilation devices disclosed herein can have multiple positions, including, but not limited to, a collapsed position, a relaxed position, a first partially dilated position, a second partially dilated position, a third partially dilated position, a fully dilated position, and a variety of positions therebetween.

In an embodiment, a dilation device of the present disclosure has a collapsed diameter sufficient to fit into any suitable sheath. In an embodiment, a dilation device of the present disclosure can fit into a retractable sheath having a diameter ranging from about 10 French (3.3 mm) to about 16 French (5.3 mm). The collapsed diameter of a dilation device of the present disclosure can be, for example, between about 3 mm and about 5 mm. In an embodiment, a dilation device of the present disclosure has a collapsed diameter of about 4.19 mm. The resting diameter of a dilatation device (relaxed state) can be, for example, between about 5 mm and about 30 mm. In an embodiment, a dilation device of the present disclosure has a resting diameter of about 25 mm. The fully expanded diameter of a dilation device of the present disclosure can be between, for example, about 10 mm and about 70 mm. In an embodiment, the collapsed diameter is slightly less than 12 french and the fully expanded diameter is between about 30 mm and about 35 mm. In an embodiment, the collapsed diameter is slightly less than 15 french and the fully expanded diameter is between about 50 mm and about 55 mm. A dilation device according to the present disclosure can also be configured to have a fully expanded diameter of 15% greater than the diameter of a vessel at the location in the vessel at which the dilation device is to be dilated. A dilation device according to the present disclosure may have any suitable length, such as any length of between about 4 cm and about 20 cm between a distal end and a proximal end when the dilation device is in a fully collapsed position. Some lengths are between about 4 cm and about 15 cm, between about 6 cm and about 15 cm, between about 8 cm and about 15 cm, between about 10 cm and about 15 cm, and between about 12 cm and about 15 cm.

A dilation device of the present disclosure may have a fully dilated expanded diameter ranging from about 10 mm to about 70 mm. Some embodiments may have a fully dilated expanded diameter between about 10 mm and about 20 mm. Some embodiments may have a fully dilated expanded diameter between about 20 mm and about 30 mm. Some embodiments may have a fully dilated expanded diameter between about 30 mm and about 40 mm. Some embodiments may have a fully dilated expanded diameter between about 40 mm and about 45 mm. Some embodiments may have a fully dilated expanded diameter between about 50 mm and about 55 mm. Some embodiments may have a fully dilated expanded diameter between about 55 mm and about 60 mm. Some embodiments may have a fully dilated expanded diameter between about 60 mm and about 70 mm. Some embodiments may have a fully dilated expanded diameter of about 50 mm. Some embodiments may have a fully dilated expanded diameter of approximately: 10 mm-18 mm, 18 mm-26 mm, 26 mm-40 mm, 40 mm-44 mm, 45 mm-48 mm, 48 mm-50 mm, 50 mm-53 mm, 53 mm-55 mm, 55 mm-57 mm, 57 mm-60 mm, 60 mm-63 mm, 63 mm-70 mm, less than 10 mm or more than 70 mm, as not all embodiments of the present disclosure are intended to be limited in this respect.

In an embodiment, a dilation device of the present disclosure includes a plurality of wires having the same or different lengths to create the dilation device. The length of the wires may effect the flexibility of the dilation device and/or the ability to provide sufficient radial force. Some embodiments may have wire lengths between about 4 cm and about 6 cm. Some embodiments may have wire lengths between about 6 cm and about 10 cm. Some embodiments may have wire lengths between about 10 cm and about 13 cm. Some embodiments may have wire lengths between about 13 cm and about 16 cm. Some embodiments may have wire lengths between about 16 cm and about 20 cm. Some embodiments may have wire lengths of about 15 cm. Some embodiments may have wires of the following approximate lengths: 4 cm-6 cm, 6 cm-8 cm, 8 cm-10 cm, 10 cm-12 cm, 12 cm-14 cm, 14 cm-16 cm, 16 cm-18 cm, 19 cm-20 cm, less than 4 cm or longer than 20 cm, as not all embodiments of the present disclosure are intended to be limited in this respect. In some embodiments, certain wires may be shorter than others to facilitate controlled expansion, adapt the expansion of the dilation device around certain locations or create a certain shape for the dilation device.

In an embodiment, a dilation device of the present disclosure may include different wire diameters as well as wires having varying lengths to create the dilation device. The wire diameter and the wire length may effect the flexibility of the dilation device and its ability to provide sufficient radial force. In some embodiments the wire diameter may range from about 0.18 mm to about 3 mm and the wire length may range from about 4 cm to about 20 cm. Some embodiments may have wire diameters ranging from about 0.13 mm to about 0.28 mm that are between about 10 cm and about 15 cm in length. Some embodiments may have wire diameters ranging from about 0.13 mm to about 0.23 mm that are between about 15 cm and about 25 cm in length. Some embodiments may have wire diameters ranging from about 0.2 mm to about 0.3 mm that are between about 14 cm to about 24 cm in length. Some embodiments may have wire diameters ranging from about 0.5 mm to about 0.6 mm that are between about 13 cm to about 23 cm in length. Some embodiments may have wire diameters ranging from about 0.7 mm to about 0.8 mm that are between about 12 cm and about 22 cm in length. Some embodiments may have wire diameters ranging from about 0.25 mm to about 1.0 mm that are between about 10 cm to about 15 cm in length. Some embodiments may have wire diameters ranging from about 0.15 mm to about 0.25 mm that are between about 6 cm and about 10 cm in length. Some embodiments may have wire diameters ranging from about 0.5 mm to about 1.5 mm that are between about 11.5 cm to about 21.5 cm in length. Some embodiments may have wire diameters ranging from about 1.0 mm to about 2.0 mm that are between about 11 cm to about 21 cm in length. Some embodiments may have wire diameters ranging from about 1.5 mm to about 2.25 mm that are between about 10.5 cm to about 20.5 cm in length. Some embodiments may have wire diameters ranging from about 1.5 mm to about 2.5 mm that are between about 10 cm and about 20 cm in length. Some embodiments may have wire diameters ranging from about 1.5 mm to about 2.5 mm that are between about 9 cm and about 19 cm in length. Some embodiments may have wire diameters ranging from about 1.5 mm to about 2.5 mm that are between about 8 cm to about 18 cm in length. Some embodiments may have wire diameters ranging from about 2.0 mm to about 2.5 mm that are between about 7 cm to about 17 cm in length. Some embodiments may have wire diameters ranging from about 1.75 mm to about 2.75 mm that are between about 6 cm to about 16 cm in length. Some embodiments may have wire diameters ranging from about 2.0 mm to about 3.0 mm that are between about 5 cm to about 15 cm in length. Some embodiments may have wire diameters ranging from about 2.0 mm to about 3.0 mm that are between about 3 cm to about 13 cm in length. Some embodiments may have wire diameters ranging from about 2.25 mm to about 3.25 mm that are between about 2 cm to about 12 cm in length. Some embodiments may have wire diameters ranging from about 2.5 mm to about 3.5 mm that are between about 1 cm and about 11 cm in length. Some embodiments may have wire diameters ranging from about 2.5 mm to about 3.5 mm that are between about 0.05 cm and about 9 cm in length. Some embodiments may have wire lengths shorter than about 4 cm or longer than about 20 cm, of diameters less than about 0.18 mm or larger than about 3 mm, as not all embodiments of the present disclosure are intended to be limited in this respect.

In an embodiment, a dilation device of the present disclosure may include wire diameters of about 0.18 mm that are about 20 cm in length. Some embodiments may have wire diameters of about 0.25 mm that are about 19 cm in length. Some embodiments may have wire diameters of about 0.20 mm that are about 7 cm in length. Some embodiments may have wire diameters of about 0.25 mm that are about 9 cm in length. Some embodiments may have wire diameters of about 0.28 mm that are about 10 cm in length. Some embodiments may have wire diameters of about 0.32 mm that are about 12 cm in length. Some embodiments may have wire diameters of about 0.55 mm that are about 18 cm in length. Some embodiments may have wire diameters of about 0.75 mm that are about 17 cm in length. Some embodiments may have wire diameters of about 1 mm that are about 16.5 cm in length. Some embodiments may have wire diameters of about 1.5 mm that are about 16 cm in length. Some embodiments may have wire diameters of about 1.75 mm that are about 15.5 cm in length. Some embodiments may have wire diameters of about 2 mm that are about 15 cm in length. Some embodiments may have wire diameters of about 2 mm that are about 14 cm in length. Some embodiments may have wire diameters of about 2 mm that are about 13 cm in diameter. Some embodiments may have wire diameters of about 2.25 mm that are about 12 cm in length. Some embodiments may have wire diameters of about 2.25 mm that are about 11 cm in length. Some embodiments may have wire diameters of about 2.5 mm that are about 10 cm in length. Some embodiments may have wire diameters of about 2.5 mm that are about 8 cm in length. Some embodiments may have wire diameters of about 2.75 mm that are about 7 cm in length. Some embodiments may have wire diameters of about 3 mm that are about 6 cm in length. Some embodiments may have wire diameters of about 3 mm that are about 4 cm in length. Some embodiments may have wire lengths shorter than 4 cm or longer than 20 cm, of diameters less than 0.18 mm or larger than 3 mm, as not all embodiments of the present disclosure are intended to be limited in this respect.

In an embodiment, a dilation device of the present disclosure may include wires having the same or different diameters to create the dilation device. The diameters of wires may effect the flexibility of the dilation device and/or the ability to provide sufficient radial force. In some embodiments, the wires have a diameter ranging from about 0.18 mm to about 3 mm. Some embodiments may have wire diameters between about 0.18 mm and about 1 mm. Some embodiments may have wires having diameters between about 1 mm and about 2 mm. Some embodiments may have wires having diameters between about 2 mm and about 3 mm. Some embodiments may have wires having diameters of about 0.28 mm. Some embodiments may have wires with diameters between about 0.20 mm and about 0.36 mm. Some embodiments may have wires of the approximate following diameters: 0.18 mm-0.25 mm, 0.25 mm-0.75 mm, 0.75 mm-1.5 mm, 1.5 mm-2 mm, 2 mm-2.5 mm, 2.5 mm-3 mm, less than 0.18 mm or more than 3 mm wires, as not all embodiments of the present disclosure are intended to be limited in this respect. For example, all or some of the wires may have a generally circular cross-section and have a diameter of between 0.008 inches and 0.018 inches. In some embodiments, a dilation device of the present disclosure includes wires of different diameters to increase or decrease the flexibility or stiffness of certain parts of the dilation device and/or to make certain portions of the dilation device thinner or thicker. In an embodiment, 25% of the wires may have a diameter of 0.28 mm, while 75% of the wires may have a diameter of 0.32 mm. In an embodiment, 50% of the wires may have a diameter of 0.35 mm, while 50% of the wires may have a diameter of 0.45 mm.

A dilation device of the present disclosure includes one or more wires to create the device. The number of wires, and the wire diameter, may effect the flexibility of the dilation device and the ability to provide sufficient radial force. In some embodiments, the number of wires may range from about 10 wires to about 100 wires and the diameter may range from about 0.18 mm to about 3 mm. Some embodiments include 10 wires that range from about 2.5 mm to about 3.5 mm in diameter. Some embodiments include 10 wires that range from about 2.0 mm to about 3.0 mm in diameter. Some embodiments include 15 wires that range from about 2.0 mm to about 3.0 mm in diameter. Some embodiments include 20 wires that range from about 1.5 mm to about 2.5 mm in diameter. Some embodiments include 25 wires that range from about 1.0 mm to about 2.0 mm in diameter. Some embodiments include 30 wires that range from about 0.5 mm to about 1.5 mm in diameter. Some embodiments include 35 wires that range from about 0.5 mm to about 1.5 mm in diameter. Some embodiments include 40 wires that range from about 0.25 mm to about 1.25 mm in diameter. Some embodiments include 45 wires that range from about 0.1 mm to about 1.0 mm in diameter. Some embodiments include 48 wires that range from about 0.1 mm to about 0.3 mm in diameter. Some embodiments include 50 wires that range from about 0.1 mm to about 0.75 mm in diameter. Some embodiments include 55 wires that range from about 0.05 mm to about 0.5 mm in diameter. Some embodiments include 65 wires that range from about 0.05 mm to about 0.5 mm in diameter. Some embodiments include 75 wires that range from about 0.05 mm to about 0.5 mm in diameter. Some embodiments include 85 wires that range from about 0.05 mm to about 0.5 mm in diameter. Some embodiments include 100 wires that range from about 0.05 mm to about 0.5 mm in diameter. Some embodiments include wire diameters less than about 0.18 mm or larger than about 3 mm in diameter, less than 10 wires or more than 100 wires, as not all embodiments of the present disclosure are intended to be limited in this respect.

In some embodiments, the wires of a dilation device of the present disclosure may change in diameter along the length of a single wire, such that a wire has a first diameter at one end and at least a second diameter somewhere else along the wire, where the first and the second diameters are different. For example, in some embodiments, the ends of a wire may have a diameter of about 0.25 mm while the middle portion of the wire may have a diameter of about 0.28 mm. In some embodiments, the diameter of the wire may change at multiple points along the wire. In some embodiments, the transition from one diameter to another may occur at a single point, thereby creating a lip. In some embodiments, the transition from one diameter to another may occur gradually along a portion of the wire. In some embodiments, the ends of the wire may have a diameter of about 0.18 mm and the middle of the wires may have a diameter of about 0.25 mm. In some embodiments, the ends of the wire may have a diameter of about 0.25 mm and the middle of the wires may have a diameter of about 1 mm. In some embodiments, the ends of the wire may have a diameter of about 1 mm and the middle of the wires may have a diameter of about 2 mm. In some embodiments, the ends of the wire may have a diameter of about 2 mm and the middle of the wires may have a diameter of about 3 mm. In some embodiments, the ends of the wire may have a diameter of about 0.25 mm and the middle of the wires have a diameter of about 0.18 mm. In some embodiments, the ends of the wire may have a diameter of about 1 mm and the middle of the wires have a diameter of about 0.25 mm. In some embodiments, the ends of the wire may have a diameter of about 2 mm and the middle of the wires have a diameter of about 1 mm. In some embodiments, the ends of the wire may have a diameter of about 3 mm and the middle of the wires have a diameter of about 2 mm. In some embodiments, the diameter of the wire may gradually increase along the length of the wire from about 0.18 mm in diameter to about 1 mm in diameter. In some embodiments, the diameter of the wire may gradually increase along the length of the wire from about 1 mm in diameter to about 2 mm in diameter. In some embodiments the diameter of the wire may gradually increase along the length of the wire from about 2 mm in diameter to about 3 mm in diameter.

The wires used in a dilation device of the present disclosure may be of any suitable size, shape, thickness and material. The dilation device may include wires arranged in any suitable pattern such as a braid pattern, coil, criss-cross, in a non-overlapping pattern in which the wires are parallel to the vessel flow path, or any other pattern as the present disclosure is not intended to be limited in this manner. The pattern of the wires may effect radial strength or device profile. For instance, the braid pattern may have greater radial force while the coil pattern may have better flexibility. It is believed that a braid in a non-overlapping pattern may help to provide the device with a low profile. In an embodiment the wires are braided in a single overlapping pattern. An example of a single overlapping pattern includes, but is not limited to, over, under, over, under, etc. In an embodiment the wires are braided in a double overlapping pattern. An example of a double overlapping pattern includes, but is not limited to, over, over, under, under, over, over, under, under, etc. In an embodiment the wires are braided in a combination of single or multiple overlapping patterns. An example of a combination pattern includes, but is not limited to, over, under, under, over, under, over, over, over, under, under, etc.

The dilation device may include wires which are predetermined to take on one or more shapes. The shape of the wires may effect the ability to properly, circumferentially mold the existing stent graft. The shape of a wire may be straight, concave, convex or bent, rounded, or curved in any way one or more times along the length of the wire, or any combination thereof. Further multiple wires having different predetermined shapes or the same predetermined shape may be combined together to form an overall shape of the dilation device. The dilation device shape may be straight, rectangular, oval, basket-like, or any other shape, as not all embodiments of the present disclosure are intended to be limited in this respect.

A dilation device of the present disclosure may include wires having a variety of shapes. The wire shape may effect the ability to achieve a low profile catheter yet provide sufficient radial force. In some embodiments, the dilation device may include round, oval, or flat wires. In some embodiments, the dilation device may include hollow wires (tubes), standard wires, or filled wires. Some embodiments may include flat wires. Some embodiments may include oval wires. Some embodiments may include round wires. Some embodiments may include hollow wires. Some embodiments may include standard wires. Some embodiments may include filled wires. Some embodiments may combine flat wires with round wires. Some embodiments may combine flat wires with both round wires and oval wires. Some embodiments may combine flat wires with oval wires. Some embodiments may combine oval wire with round wires. Some embodiments may include oval hollow wires. Some embodiments may include flat hollow wires. Some embodiments may include flat filled wires. Dilation devices may include other wire shapes and combinations as not all embodiments of the present disclosure are intended to be limited in this respect. A dilation device according to the present disclosure may have any suitable density of wires and the wires may be formed in any suitable pattern, such as in a braided pattern, a criss-cross pattern, or in a non-overlapping pattern in which the wires are parallel to vessel flow path. Alternatively, all or some of the wires may include one or more struts that have a thickness of between about 0.008" and 0.018" and a width of between 0.020" and 0.050".

If a dilation device of the present disclosure has wires that are parallel (as used in this context, "parallel" means the wires are substantially parallel to one another) to the vessel flow path, the dilation device may have between four and twenty-four wires, or may have more than twenty-four wires. In various embodiments, a dilation device according to the present disclosure includes, respectively, four wires, five wires, six wires, seven wires, eight wires, nine wires, ten wires, eleven wires, twelve wires, thirteen wires, fourteen wires, fifteen wires, sixteen wires, seventeen wires, eighteen wires, nineteen wires, twenty wires, twenty-one wires, twenty-two wires, twenty-three wires and twenty-four wires. The maximum distance between each wire in such a dilation device can vary depending upon the number of wires, the width of the wires and the proposed use of the dilation device, but generally the maximum distance between wires will be between about 1 mm and about 100 mm when the device is fully dilated. In various embodiments of the dilation device, the maximum distance is, respectively, no greater than about 1 mm, 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm or 100 mm.

A dilation device of the present disclosure may include a spacing area between the wires. The spacing area may effect the ability of fluid to flow into and throughout the vessels. In some embodiments, the spacing area may be constructed such that at least some of the spaces between the wires in a body portion of the dilation device are larger than the spaces between the wires at a distal end or a proximal end when the dilation device is dilated within a vessel, so as to allow fluid to flow into side vessels if the dilation device is positioned against a side vessel. In an embodiment, the dilation device has a spacing area ranging from about 0.5 mm$^2$ to about 5 mm$^2$. The dilation device may have a spacing area of no less than about 0.5 mm$^2$ when the dilation device is dilated. The dilation device may have a spacing area ranging from about 0.5 mm$^2$ and about 1 mm$^2$ when the dilation device is dilated. The dilation device may include a spacing area ranging from about 1 mm$^2$ and about 1.5 mm$^2$ when the dilation device is dilated. The dilation device may include a spacing area ranging from about 1.5 mm$^2$ and about 2 mm$^2$ when the dilation device is dilated. The dilation device may include a spacing area ranging from about 2 mm$^2$ and about 2.5 mm$^2$ when the dilation device is dilated. The dilation device may include a spacing area ranging from about 2.5 mm$^2$ and about 4 mm$^2$ when the dilation device is dilated. The dilation device may include a spacing area ranging from about 4 mm$^2$ and about 5 mm$^2$ when the dilation device is dilated. Some embodiments may have a wire spacing area of about: 0.5 mm$^2$-1.2 mm$^2$, 1.2 mm$^2$-2.7 mm$^2$, 2.7 mm$^2$-3 mm$^2$, 3 mm$^2$-3.5 mm$^2$, 3.5 mm$^2$-4.1 mm$^2$, 4.1 mm$^2$-5 mm$^2$, less than 0.5 mm$^2$ or more than 5 mm$^2$, as not all embodiments of the present disclosure are intended to be limited in this respect. In an embodiment, the dilation device has a spacing area of no less than 0.5 mm$^2$ when the dilation device is dilated.

The spacing area between the wires can change as the dilation device expands and contracts. In some embodiments, the spacing area may become larger as the dilation device is expanded and the spacing area may decrease as the dilation device is collapsed.

If a dilation device according to the present disclosure includes wires in a criss-cross pattern, each of the largest spaces between the wires when the dilation device is fully dilated could have an area of between about 1 mm$^2$ and about 400 mm$^2$, including areas of about 1 mm$^2$, 2 mm$^2$, 4 mm$^2$, 10 mm$^2$, 25 mm$^2$, 50 mm$^2$, 75 mm$^2$, 100 mm$^2$, 150 mm$^2$, 200 mm$^2$, 250 mm$^2$, 300 mm$^2$, 350 mm$^2$, and/or 400 mm$^2$ or areas within that range. It is also possible that the area of the largest spaces could be larger than about 400 mm$^2$ or smaller than about 1 mm$^2$, as long as the dilation device works for the intended purpose of dilating a vessel or dilating a structure within a vessel without occluding or substantially hindering fluid flow through the vessel.

A dilation device according to the present disclosure may also have spaces between the wires that are greater in the central portion of the dilation device than at the ends of the dilation device. A dilation device of the present disclosure may include wires that are braided having multiple braid densities at different areas of the braid. The braid density may effect the flexibility of the dilation device and the ability to provide sufficient radial force. For instance, a greater density may decrease the flexibility of that portion of the dilation device, but increase the ability of that portion to provide radial force while a smaller density may increase the flexibility of that portion of the dilation device, but decrease the ability of that portion to provide radial force. In some embodiments, the density of wires may range from about 2 ppi (picks per inch) to about 19 ppi, which is the number of wire crossovers per inch of shaft. Some embodiments may have wire densities between about 2 ppi and about 5 ppi. Some embodiments may have wire densities between about 5 ppi and about 8 ppi. Some embodiments may have wire densities between about 8 ppi and about 11 ppi. Some embodiments may have wire densities between about 11 ppi and about 14 ppi. Some embodiments may have wire densities between about 14 ppi and about 19 ppi. Some embodiments may have wire densities of about 7 ppi. Some embodiments may have devices formed of a certain number of wires of about the following wire densities: 3 ppi-5 ppi, 5 ppi-7 ppi, 7 ppi-9 ppi, 9 ppi-11 ppi, 11 ppi-13 ppi, 13 ppi-15 ppi, 15 ppi-17 ppi, 17 ppi-19 ppi, less than 2 ppi or more than 19 ppi, as not all embodiments of the present disclosure are intended to be limited in this respect. In an embodiment, a dilation device of the present disclosure may be formed of about 48 wires at a density ranging from about 6 ppi to about 8 ppi.

In an embodiment, a dilation device of the present disclosure includes wires that are braided and secured to a catheter at a first connection point and at a second connection point that is distally located from the first connection point In an embodiment, a dilation device is defined by the number of wires that form the braid and the number of helical-shaped turns about the longitudinal axis of the catheter that each wire makes from one connection point to the other. In an embodiment, the number of wires used to make the braid is 48 and each wire makes approximately one helical-shaped turn from one connecting point to the other. In an embodiment, the number of wires used to make the braid is 10 and each wire makes approximately 5 helical-shaped turns from one connecting point to the other. In an embodiment, up to 100 wires are used to make the braid with each wire making approximately one half helical-shaped turns from one connecting point to the other. In addition, the wires forming the braid can have a variety of different shapes, including, but not limited to, round, square, flat, hollow, solid, and filled wire shapes.

A dilation device of the present disclosure may include a braid made from a variety of materials. The wire material may effect the ability to achieve a low profile catheter yet provide sufficient radial force. In an embodiment, a dilation device of the present disclosure is made of a shape memory alloy or a shape memory polymer. In some embodiments the dilation device is made of Nitinol, plastic, stainless steel, Elgiloy, cobalt chromium or any suitable metal, plastic, or any other material as the present disclosure is not intended to be limited in this respect. In some embodiments, a braid can be made from a combination of materials to allow for varying properties. A wire may be comprised of stainless steel, nitinol, cobalt, chromium or any suitable metal, plastic or other suitable material. In an embodiment, the wire is comprised of nitinol, has a generally circular cross section and a diameter of about 0.19 mm to about 0.4 mm.

In an embodiment, a dilation device according to the present disclosure exerts a radial force when being dilated, wherein the radial force is sufficient to dilate a stent or stent graft with which the dilation device is used. The radial pressure can be between about 1 pound per square inch (psi) and 20 psi, between 6 psi and 20 psi, between 7 psi and 20 psi, between 8 psi and 20 psi, between 9 psi and 20 psi, between 10 psi and 20 psi or between 15 psi and 20 psi. The radial pressure can be between about 1 pound per square inch (psi) and 10.5 psi, between 3 psi and 10.5 psi, between 5 psi and 10.5 psi, between 7 psi and 10.5 psi or between 9 psi and 10.5 psi. The radial pressure may vary within a given range depending upon the diameter of the device (e.g., the radial pressure may decrease as the diameter of the device increases). The radial pressure within a given, suitable psi range is preferably exerted over the entire working range of the device. The "working range" means all diameters of the device at which the device is expanding a stent or stent graft. In an embodiment, the measured radial force exerted at given diameters was 9.4 psi at a diameter of 20 mm, 6.7 psi at a diameter of 30 mm and 6.3 psi at a diameter of 40 mm. A dilation device according to the disclosure preferably exerts a radial pressure of between 0 psi and 10.5 psi over at least part, and preferably over all, of its working range. In an embodiment, a dilation device according to the present disclosure exerts no radial force when being dilated.

Some dilation devices according to the disclosure are also sufficiently compliant (or flexible) so that when placed in a vessel and dilated the device conforms to the dimensions of the vessel even when the vessel dimensions are not uniform. Some of the dilation devices of the present disclosure can conform to one or more diameter disparity ratios of between approximately 1.2:1 and 3.4:1. Some of the dilation devices of the present disclosure can conform to one or more diameter disparity ratios of between approximately 1.2:1 and 13:1. Some of the dilation devices of the present disclosure can conform to one or more diameter disparity ratios of between approximately 1.2:1 and 20:1. The diameter disparity ratio may be between approximately 2:1 and 4:1. The diameter disparity ratio may be between approximately 4:1 and 5.5:1. The diameter disparity ratio may be between approximately 5.5:1 and 6.5:1. The diameter disparity ratio may be between approximately 6.5:1 and 8:1. The diameter disparity ratio may be between approximately 8:1 and 10:1. The diameter disparity ratio may be between approximately 10:1 and 13:1. The diameter disparity ratio may be between approximately 13:1 and 15:1. The diameter disparity ratio may be between approximately 15:1 and 18:1. The diameter disparity ratio may be between approximately 18:1 and 20:1. The diameter disparity ratio may be less than 1.2:1 or more than 13:1, as not all embodiments of the present disclosure are intended to be limited in this respect. Some dilation devices according to the present disclosure can conform to one or more multi-vessel diameter disparity ratios of between approximately 1.2:1 and 5:1. The multi-vessel diameter disparity ratio may be between approximately 1.2:1 and 3.4:1.

A dilation device according to the disclosure may be constructed to any suitable size or in any suitable manner to accommodate a particular vessel, including veins and arteries (e.g., the abdominal aorta, aortic arch, the ascending aorta, the descending aorta, an iliac artery, or a renal artery). For example, the dilation device may be used in wall apposition of a thoracic and/or abdominal endoluminal grafts, which means the dilation device expands to position at least a portion of a stent graft snugly (without a sheath) against the artery wall.

A dilation device may be introduced into a vessel using either a biaxial (without a sheath) or triaxial (with a sheath) catheter, which is typically inserted over a guide wire. Optionally, the dilation device includes one or more radio-opaque markers or bands that assist an operator in locating the dilation device once in a vessel, although a dilation device according to the disclosure can generally be seen using fluoroscopy without the need for radio-opaque markers or bands.

When dilated, a dilation device according to the disclosure does not occlude or substantially hinder the flow of fluid through a vessel or into a side vessel because the fluids flow through the spaces (or openings) between the wires. In a pressure monitoring test using water as the fluid and a plastic tube to simulate the aorta the pressure drop within a vessel and downstream of a dilated dilation device as generally shown in FIGS. 13-20 was measured as less than 1%. This test measured the flow lengthwise through the dilation device, wherein the water had to flow through both the proximal end and distal end of the dilation device. Thus, the water had to flow through the smallest openings in the dilation device, which in the embodiment tested were located at the distal end and the proximal end. It is therefore believed that flow into a side vessel, wherein fluid would flow through the smaller openings in the distal end of the dilation device and then through larger openings in the body portion of the dilation device and into the side vessel, would be less hindered than flow lengthwise through the dilation device. Accordingly, the pressure drop due to the dilation of a dilation device according to the disclosure, either measured downstream of the proximal end of the device or measured in a side vessel covered by the dilation device (such as when the dilation device is in the aorta and covers one or both renal arteries), would be less than 70%, less than 60%, less than 50%, less than 40%, less than 30%, less than 20%, less than 10%, less than 5%, less than 2%, and/or less than 1%. In an embodiment, the pressure drop due to the dilation of a dilation device according to the disclosure, either measured downstream of the proximal end of the dilation device or measured in a side vessel covered by the dilation device, is negligible. In both in vivo and in vitro pressure monitoring tests using standard aortic blood pressure measuring equipment, a pressure drop within a vessel and downstream of a dilated dilation device as generally shown in FIGS. 28 and 29 was not detectable.

In an embodiment, a dilation device of the present disclosure has 48 round solid nitinol wires having a braided configuration, wherein each of the wires has a diameter of about 0.28 mm, a length of about 15 cm, a braid density of about 7 ppi, and a space between wires of about 3 mm$^2$. The dilation device in such an embodiment has a fully expanded outer diameter of about 55 mm, and a collapsed diameter of about 4.7 mm. The dilation device can be used with a vessel having a diameter disparity ratio of 10:1. In an embodiment, a kink radius of the dilation device is about 2 inches (~51 mm) in a relaxed state. In an embodiment, a kink radius of the dilation device is about 2 inches (~51 mm) in a dilated state.

In an embodiment, a dilation device of the present disclosure has between about 40 to about 60 flat hollow stainless steel wires having a braided configuration, wherein each of the wires has a diameter ranging from about 0.20 mm to about 0.30 mm, a length ranging from about 13 cm to about 17 cm, a braid density ranging from about 5 ppi to about 9 ppi, and a space between wires ranging from about 2.0 mm$^2$ to about 4.0 mm$^2$. The dilation device in such an embodiment has a fully expanded outer diameter ranging from about 50 mm to about 60 mm, and a collapsed diameter ranging from about 4.3 mm to about 4.9 mm. The dilation device can be used with a vessel having a diameter disparity ratio of between about 8:1 and about 12:1. In an embodiment, a kink radius of the dilation device is between about 2 inches (~51 mm) and about 4 inches (~102 mm) in a relaxed state. In an embodiment, a kink radius of the dilation device is between about 2 inches (~51 mm) and about 4 inches (~102 mm) in a dilated state.

In an embodiment, a dilation device of the present disclosure has between about 30 to about 70 oval solid cobalt chromium wires having a straight configuration, wherein each of the wires has a diameter ranging from about 0.10 mm to about 0.5 mm, a length ranging from about 10 cm to about 20 cm, a density (a product of the number of wires and the length of the wires) ranging from about 3 ppi to about 12 ppi, and a space between wires ranging from about 0.5 mm$^2$ to about 7 mm$^2$. The dilation device in such an embodiment has a fully expanded outer diameter ranging from about 30 mm to about 80 mm, and a collapsed diameter ranging from about 3.5 mm to about 5.4 mm. The dilation device can be used with a vessel having a diameter disparity ratio of between about 5:1 and 15:1. In an embodiment, a kink radius of the dilation device is between about half-an-inch (~12.7 mm) and about 5 inches (127 mm) in a relaxed state. In an embodiment, a kink radius of the dilation device is between about half-an-inch (~12.7 mm) and about 5 inches (127 mm) in a dilated state.

In an embodiment, a dilation device of the present disclosure has 75 wires, round solid nitinol wires having a braided configuration, wherein each of the wires has a diameter of about 0.18 mm, a length of about 10 cm, a braid density of about 10 ppi, and a space between wires of about 1 mm$^2$. The dilation device in such an embodiment has a fully expanded outer diameter of about 65 mm, and a collapsed diameter of about 5.3 mm. The dilation device can be used with a vessel having a diameter disparity ratio of 13:1. In an embodiment, a kink radius of the dilation device is about 3 inches (~76.2 mm) in a collapsed position. In an embodiment, a kink radius of the dilation device is about 3 inches (~76.2 mm) in an expanded position.

In an embodiment, a dilation device of the present disclosure has between about 65 and about 85 oval hollow stainless steel wires having a braided configuration, wherein each of the wires has a diameter ranging from about 0.15 mm to about 0.20 mm, a length ranging from about 8 cm to about 12 cm, a braid density ranging from about 8 ppi to about 12 ppi, and a space between wires ranging from about 0.5 mm$^2$ to about 1.5 mm$^2$. The dilation device in such an embodiment has a fully expanded outer diameter ranging from about 60 mm to about 70 mm, and a collapsed diameter ranging from about 4.5 mm to about 5.8 mm. The dilation device can be used with a vessel having a diameter disparity ratio of between about 11:1 and 14:1. In an embodiment, a kink radius of the dilation device is between about 2 inches (~51 mm) to about 4 inches (~102 mm) in a collapsed position. In an embodiment, a kink radius of the dilation device is between about 2 inches (~51 mm) to about 4 inches (~102 mm) in an expanded position.

In an embodiment, a dilation device of the present disclosure has between about 50 to about 100 round solid cobalt chromium wires in a straight configuration, wherein each of the wires has a diameter ranging from about 0.10 mm to about 1.0 mm, a length ranging from about 5 cm to about 17 cm, a density (a product of the number of wires and the length of the wires) ranging from about 5 ppi to about 15 ppi, and a space between wires ranging from about 0.25 mm$^2$ and 3 mm$^2$. The dilation device in such an embodiment has a fully expanded outer diameter ranging from about 50 mm to about 90 mm, and a collapsed diameter ranging from about 3.3 mm to about 6.6 mm. The dilation device can be used with a vessel having a diameter disparity ratio between about 5:1 and 17:1. In an embodiment, a kink radius of the dilation device is between about half-an-inch (~12.7 mm) to about 5 inches (127 mm) in a relaxed state. In an embodiment, a kink radius of the dilation device is between about half-an-inch (~12.7 mm) to about 5 inches (127 mm) in a dilated state.

In an embodiment, a dilation device of the present disclosure has 25 round solid nitinol wires having a braid configuration, wherein each of the wires has a diameter of about 0.38 mm, a length of about 20 cm, a braid density of about 4 ppi, and a space between wires of about 5 mm$^2$. The dilation device in such an embodiment has a fully expanded outer diameter of about 45 mm, and a collapsed diameter of about 3.8 mm. The dilation device can be used with a vessel having a diameter disparity ratio of 8:1. In an embodiment, a kink radius of the dilation device is about 1 inch (~25.4 mm) in a collapsed position. In an embodiment, a kink radius of the dilation device is about 1 inch (~25.4 mm) in an expanded position.

In an embodiment, a dilation device of the present disclosure has between about 20 to about 30 hollow stainless steel wires having a braided configuration, wherein each of the wires has a diameter ranging from about 0.35 mm to about 0.40 mm, a length ranging from about 18 cm to about 22 cm, a braid density ranging from about 3 ppi to about 5 ppi, and a space between wires ranging from about 4 mm$^2$ and 6 mm$^2$. The dilation device in such an embodiment has a fully expanded outer diameter ranging from about 40 mm to about 50 mm, and a collapsed diameter ranging from about 3.56 mm to about 4.0 mm. The dilation device can be used with a vessel having a diameter disparity ratio of between about 7:1 to 9:1. In an embodiment, a kink radius of the dilation device is between about half-an-inch (~12.7 mm) and about and one-and-a-half inches (38.1 mm) in a collapsed position. In an embodiment, a kink radius of the dilation device is between about half-an-inch (~12.7 mm) and about and one-and-a-half inches (38.1 mm) in an expanded position.

In an embodiment, a dilation device of the present disclosure has between about 10 to about 50 round solid cobalt chromium wires having a straight configuration, wherein each of the wires has a diameter ranging from about 0.25 mm to about 0.50 mm, a length ranging from about 15 cm to about 25 cm, a density (a product of the number of wires and the length of the wires) ranging from about 1.5 ppi to about 6.5 ppi, and a space between wires ranging from about 2 mm$^2$ and 8 mm$^2$. The dilation device in such an embodiment has a fully expanded outer diameter ranging from about 25 mm to about 65 mm, and a collapsed diameter ranging from about 2.54 mm to about 5.08 mm. The dilation device can be used with a vessel having a diameter disparity ratio of between about 4:1 to 12:1. In an embodiment, a kink radius of the dilation device is between about one quarter of an inch (6.35 mm) and about three inches (76.2 mm) in a relaxed state. In an embodiment, a kink radius of the dilation device is between about one quarter of an inch (6.35 mm) and about three inches (76.2 mm) in a dilated state.

Figure 1A:
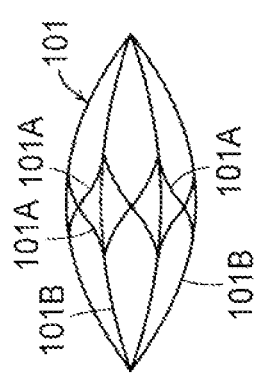
FIG. 1A shows a side view of an embodiment of a dilation device.
Figure 1B:
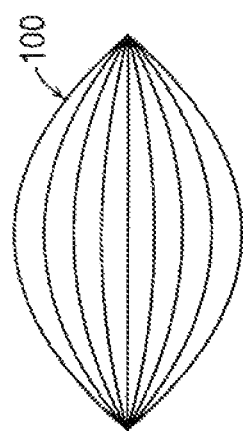
FIG. 1B shows a side view of an embodiment of a dilation device.

Reference will now be made to embodiments of the disclosure, examples of which are illustrated in the accompanying drawings, wherein the purpose is to describe certain examples of the disclosure and not to limit the scope of the claims. In an embodiment, the dilation devices of the present disclosure are dilated and collapsed by winding (to contract) and unwinding (to dilate) a plurality of wires. In an embodiment, the wires are formed in a spiraled pattern. FIG. 1A shows an embodiment of a dilation device 100 in a dilated position. The dilation device 100 is generally oval-shaped and may be spiraled. FIG. 1B shows an embodiment of a dilation device 102. The dilation device 102 has a substantially-linear section "A" of wires in the middle of the dilation device 102, while the wires in end sections "B1" and "B2" are at an angle so that the wires converge at approximately the same point at each respective end 102A, 102B on either side of the dilation device 102. In this way, section A of the dilation device 102 may exert more even pressure against a vessel and/or structure within a vessel. In this example, the substantially-straight section A is approximately 3 cm in length, while each of the end sections B1 and B2 is approximately 1 cm in length. However, the dilation device 102 may be of any suitable size or shape and be constructed in any manner.

Figure 1D:
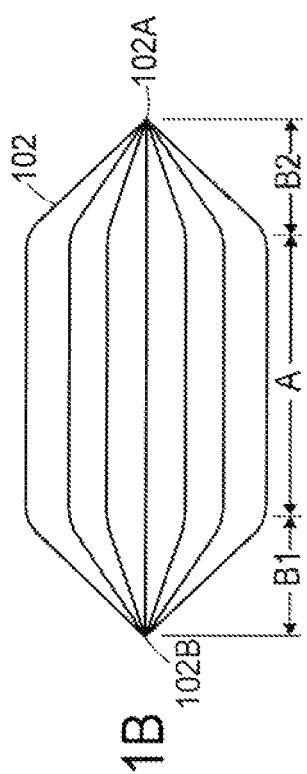
FIG. 1D shows a side view of an embodiment of a dilation device.

FIG. 1D shows an embodiment of a dilation device 101 in a dilated position. The dilation device 101 is spiraled, and includes support members 101A between wires 101B. The support members 101A provide additional strength to the dilation device 101.

Figure 1C:
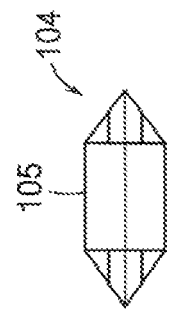
FIG. 1C shows a side view of an embodiment of a dilation device.

Dilation device 103 shown in FIG. 1C is an exaggerated view of wires in a spiraled dilation device such as device 100 when the wires are in a spiraled position. In this position, the diameter of the dilation device is reduced, allowing for insertion into a blood vessel. Unspiraling the wires causes the device 103 to dilate. Other embodiments of a spiraled dilation device will be discussed further with regard to FIGS. 2A-C and FIGS. 3A-D.

Figure 1E:
FIG. 1E shows an embodiment of a lining that can be used with any of the dilation devices disclosed herein.

Any dilation device according to the present disclosure may utilize a lining, such as lining 105 shown in FIG. 1E. A lining such as lining 105 may be positioned on part of the exterior surface and/or interior surface of a dilation device, such as dilation device 104. The use of lining 105 (a) provides a more even surface (depending upon the nature of the device with which the device is used) for exerting pressure during the dilation process, and/or (b) helps to prevent the wires of the device from becoming entangled with exposed wires on a stent or stent graft.

Lining 105 is preferably made from a permeable material, which would be important if the lining 105 is positioned such that the lining 105 could occlude or seriously hinder blood flow. However, impermeable materials may used if the lining 105 is not positioned where the lining 105 could seriously hinder blood flow. For example, in dilation device 104, even if an impermeable material is used for the lining, blood will still flow through the gaps between the wires at each end of the dilation device 104. So as long as the dilation device 104 is not positioned so that the dilation device 104 blocks a side vessel or an impermeable membrane on the dilation device 104 is not positioned so that the dilation device 104 blocks a side vessel, an impermeable material could be used. Any suitable material may be used for the liner 105 and examples of preferable lining materials include, but are not limited to, polyurethane, PTFE (polytetrafluoroethylene), nylon, or any material used in carotid embolic protection devices.

Figure 2A:
FIG. 2A shows a side view of an embodiment of a dilation device in a first position.
Figure 2C:
FIG. 2C shows a sectional view taken along line 2C-2C of FIG. 2B of the dilation device of FIG. 2B.
Figure 2B:
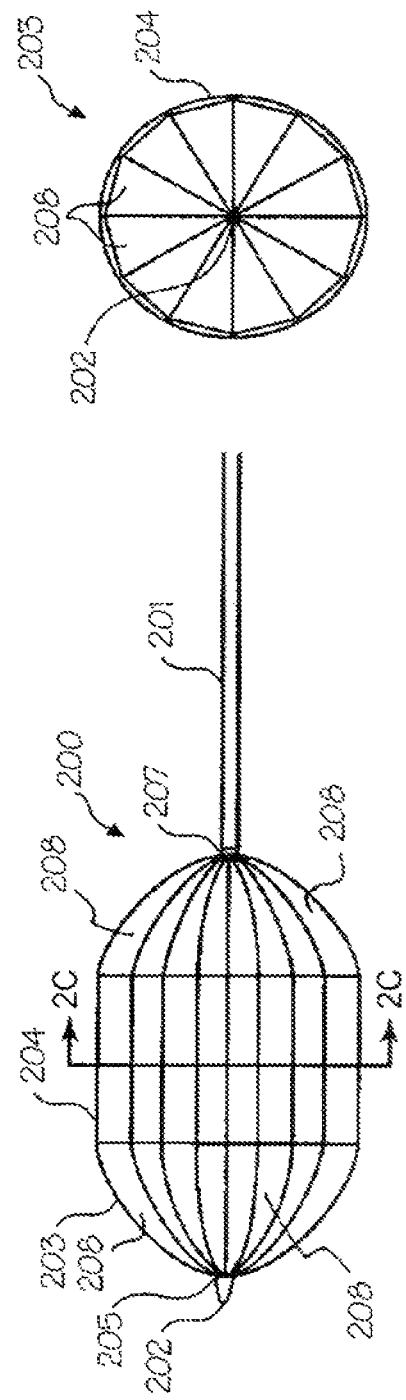
FIG. 2B shows a side view of the dilation device of FIG. 2A in an expanded position.

FIGS. 2A-C show an assembly 200 according to an embodiment of the disclosure. FIG. 2A shows a dilation device 203 in a first position for insertion into a blood vessel. Assembly 200 also includes a biaxial catheter 201 (biaxial catheter does not include a catheter sheath) with a distal tip 202. Catheter 201 (and any catheter used with a device as described or claimed herein) may be made of any material suitable for insertion into a vessel and may be sized for a particular vessel. Catheter 201 has an outer tube 201A, a central tube (not shown) running the length of the catheter. The central tube includes a wire port (not shown) in distal tip 202 and a lumen (not shown) for receiving a guide wire. Catheter 201 is inserted into a vessel by being guided over a guide wire going through the wire port and through the lumen in the central tube. Catheter 201 may be triaxial, in which case there would be a catheter sheath over device 203 (as described below).

Dilation device 203 is affixed to catheter 201 at point 205 and also at point 207. As shown in FIG. 2A, dilation device 203 is spiraled around the central tube in catheter 201 in a first position. In this position, catheter 201 and dilation device 203 are positioned to be inserted into the vessel. Dilation device 203 may optionally include a lining 204, which may be one of the same types of linings as discussed above.

FIG. 2B shows device 203 in an expanded position. Dilation device 203 is expanded by exerting a twisting motion on either outer tube 201A (preferred) or on the central tube, while keeping the other of the two tubes relatively still so that device 203 can expand. Because dilation device 203 is affixed at point 205 to the central tube and at point 207 to outer tube 201A, a twisting motion applied to outer tube 201A, while keeping the central tube relatively still (at least with as little motion as necessary to allow device 203 to expand), will unspiral and dilate device 203. Optionally, the twisting motion will be applied to the central lumen.

FIG. 2C shows a cross-sectional view taken along line 2C-2C when dilation device 203 is in an expanded position. As can be seen, lining 204 provides for a more substantially uniform surface than would the wire mesh of dilation device 203 alone. Gaps 208 between the wires of dilation device 203 allow fluid to flow through device 203.

FIGS. 3A-3D show additional views of an assembly including a spiraled dilation device according to one embodiment of the disclosure. FIG. 3A shows a spiral mesh structure rather than the straighter, cage-like structure of FIGS. 2A-C. The spiral mesh shown in FIGS. 3A-3D has a greater wire density when expanded than the structure shown in FIGS. 2A-C. The wire density (i.e., the number of wires in a given area) used in a dilation device may be varied for different applications. In general, the denser the wire mesh when a device is dilated, the more surface area available to press against a blood vessel and/or structure within the blood vessel.

FIG. 3A shows dilation device 303a in an expanded position and in a non-expanded position. FIG. 3B shows an assembly 350 including an expanded spiral mesh device 353 and catheter 351. Device 353 is affixed to catheter 351 at affixation points 355 and 357. Catheter 351 also has a distal tip 352.

FIG. 3C shows a partial, sectional side view of an assembly 360 with a dilation device 363 having a wire mesh structure, and a catheter 361 with a distal tip 362. While not necessary, a tapered front end on distal tip 362 allows for easier insertion into a vessel. At the end of distal tip 362 is a wire port 366, which leads to a lumen, for insertion of catheter 361 over a guide wire 370. The proximal end of distal tip 362 may have a reverse taper towards affixation point 365. Affixation point 365 is the point at which the distal end of dilation device 363 connects to central tube 364. Affixation point 365 is the point at which the proximal end of dilation device 303 connects to outer tube 369, which is positioned coaxially around central tube 364. Dilation device 363 is expanded by twisting outer tube 369 (or alternatively by twisting central tube 364).

FIG. 3D shows a front view of device 350, which was previously described.

FIGS. 4A-C show an assembly 400 having a non-spiraled, expansive dilation device according to one embodiment of the disclosure. FIG. 4A shows a non-spiraled, dilation device 403 in a first position for insertion into a blood vessel. Assembly 400 also includes a catheter 401 with a distal tip 402. Catheter 401 may be any device having a central lumen and being capable of insertion into a blood vessel over a guide wire. Catheter 401 has a central tube (not shown) with a wire port (not shown) in distal tip 402 that communicates with a lumen in the central tube. Catheter 401 is inserted into a blood vessel over a guide wire going through the wire port and into the lumen.

Dilation device 403 is affixed to catheter 401 at point 405 and also at point 407. As shown in FIG. 4A, dilation device 403 is not spiraled. That is, each wire of dilation device 403 is substantially parallel to the other wires and runs in a substantially straight line from affixation point 405 (on a central tube, which is not shown) to affixation point 407 on outer tube 401A. In this first position shown in FIG. 4A, the catheter 401 and dilation device 403 are insertable into a vessel. Dilation device 403 may optionally include a lining 404 as discussed above with reference to FIG. 1, which in this embodiment is on the inside surface of dilation device 403.

FIG. 4B shows device 400 in an expanded position. Dilation device 403 is expanded by exerting linear pressure via catheter 401 (e.g., a push-pull motion). Because dilation device 403 is affixed at points 405 and 407, a linear motion applied to one tube of catheter 401 (such as by pulling the central tube or pushing outer tube 401A) will expand device 403. As can be seen in FIG. 4B, the use of optional lining 404 creates a substantially uniform surface for dilating blood vessels and structures.

FIG. 4C shows a sectional view taken along line 4C-4C when dilation device 403 is in the expanded position. Gaps 408 between the wires of dilation device 403 allow fluid to flow through device 403.

Figure 5A:
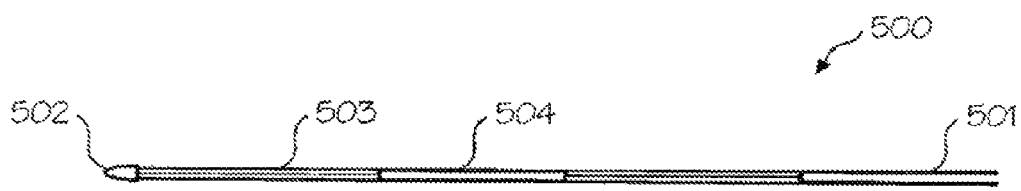
FIG. 5A shows a partial, side view of a dilation device of the present disclosure in a collapsed position.
Figure 5B:
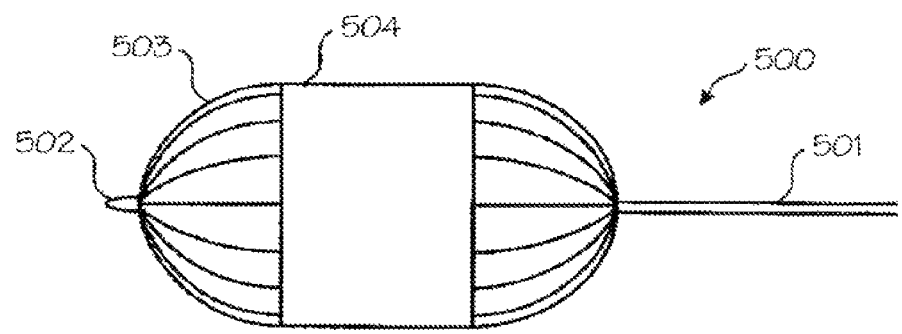
FIG. 5B shows a partial, side view of the dilation device of FIG. 5A in an expanded position.

FIG. 5 shows assembly 500 including a non-spiraled, expansive dilation device 503 according to one embodiment of the disclosure. Assembly 500 also includes a catheter 501 having a distal tip 502. Assembly 500 has the same structure as assembly 400 except that liner 504 is placed on the outside of dilation device 503. FIG. 5A shows the dilation device 503 in a collapsed position. FIG. 5B shows the dilation device 503 in an expanded position.

Figure 6A:
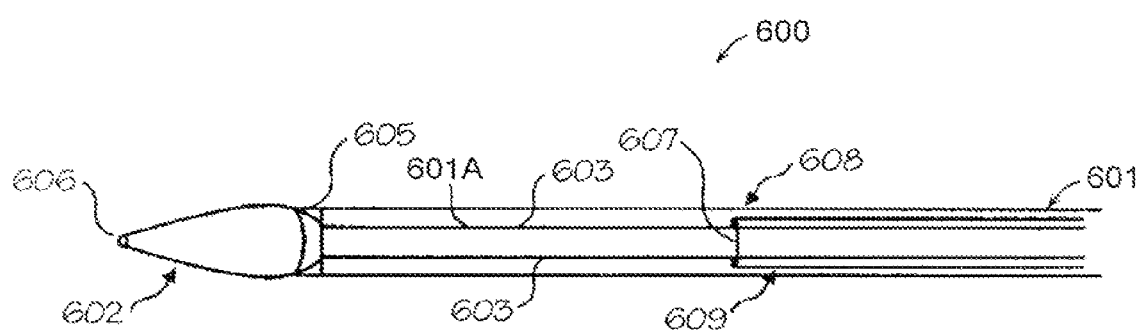
FIG. 6A shows a partial, side view of an embodiment of a delivery and deployment system for a dilation device of the present disclosure, with the dilation device in a collapsed position within the delivery and deployment system.
Figure 6B:
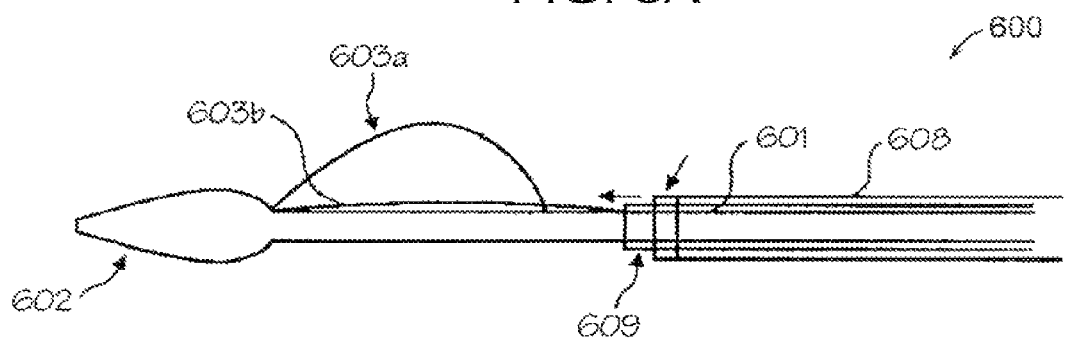
FIG. 6B shows a partial, side view of the delivery and deployment system of FIG. 6A, with the dilation device in two positions within the delivery and deployment system.

FIGS. 6A-B show an assembly 600 for a non-spiraled, dilation device according to an embodiment of the disclosure. Triaxial catheter 601 includes a central tube 601A, an outer tube 609 and a catheter sheath 608. Wire port 606 may be constructed to fit over any size guide wire (e.g., port 606 may be a 0.038" diameter wire port). Affixation point 605 is where the distal end of dilation device 603 attaches to central tube 601A. Outer tube 609 is positioned coaxially around central tube 601A and the proximal end of dilation device 603 attaches to outer tube 609 at affixation point 607. Catheter sheath 608 is positioned coaxially around outer tube 609 and can be moved towards tip 602 to cover device 603 or away from tip 602 to expose device 603. Catheter sheath 608 may include radiopaque markers to indicate when device 603 has cleared the treatment zone.

FIG. 6B shows dilation device 603 in two positions. In position 603a, dilation device 603 is expanded. The expansion is accomplished by pushing or otherwise moving (such as by using a screw mechanism) outer tube 609 forward (preferred) while keeping central tube 601A relatively stationary or central tube 601A backward while keeping outer tube 609 relatively stationary. In this manner the proximal end of dilation device 603 and the proximal end of dilation device 603 are moved towards each other and the wires of dilation device 603 expand outward. In position 603b, the wires of dilation device 603 remain at essentially their smallest diameter and close to central tube 601A. If the device 603 had been expanded, the device 603 is moved to the position shown in position 603b by increasing the distance between the distal end and proximal end of device 603 by either pulling outer tube 609 back or pushing central tube 601A forward.

Figure 7:
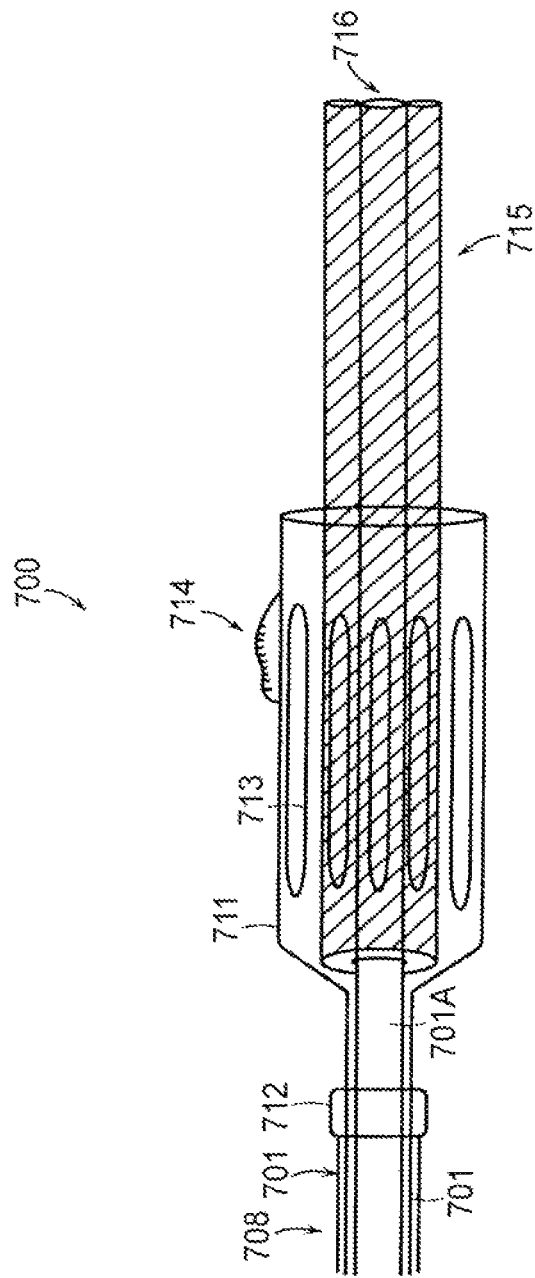
FIG. 7 shows an embodiment of a control mechanism for use with a dilation device of the present disclosure.

FIG. 7 shows a control mechanism 700 for a dilation device according to one embodiment of the disclosure. Control mechanism 700 is the hand-held portion of a dilation assembly (which in this embodiment is a catheter that includes the controls and the device) and may be used with both spiraled and non-spiraled dilation devices. In the case of a non-spiraled, dilation device, handle 711 is attached to catheter sheath 708 through hemostatic valve 712. For both spiraled and non-spiraled dilation devices, central tube 701A of catheter 701 runs through handle 711 and has a wire port 716 at its distal end that communicates with a lumen.

As shown in FIG. 7, handle 711 is a nut-type handle that is either fused to an outer sheath and may be twisted (for a spiraled dilation device) or pushed/pulled (for a non-spiraled, expansive dilation device) to engage or disengage a dilation device. Handle 711 may include surface texturing 713 for easier grip. Handle 711 may also include a threaded, bolt-type fixation handle 715 that is fused to catheter 701. This allows for execution of a twisting motion for spiraled dilation devices. Handle 711 may also include a thumb-controlled quick release 714. Quick release 714 disengages handle 711 from the bolt-type fixation handle, allowing push/pull motions to be exerted on the handle and any attached sheaths and/or catheters (e.g., for engaging non-spiraled dilation devices).

Figure 8:
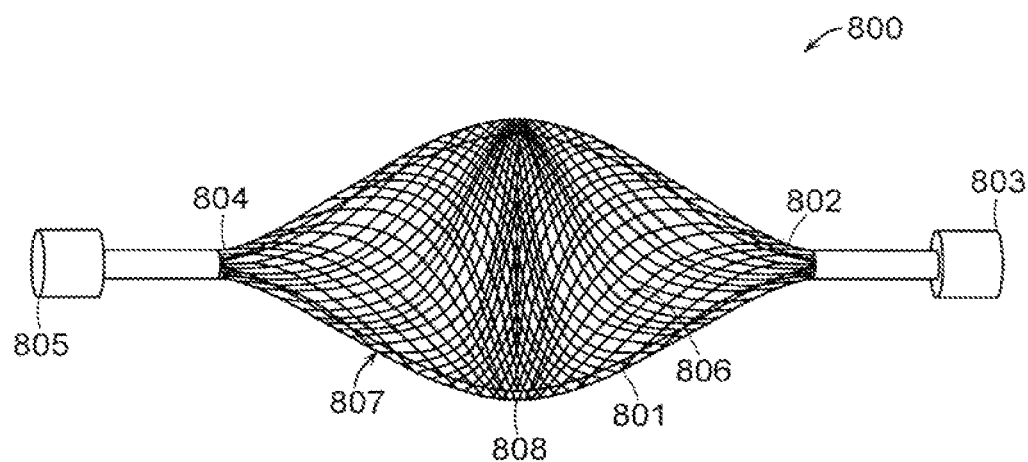
FIG. 8 is a side view of an embodiment of a dilation device of the present disclosure in a dilated position.

FIG. 8 shows an alternate device 800 according to the disclosure that is shown in a dilated position. Device 800 is comprised of wires 801 and includes a proximal end 802 retained by a retention member 803 and a distal end 804 retained by a retention member 805. As used herein, the distal end 804 and the proximal end 802 are the parts of the device that extend about 15 mm from each respective retention member. Device 800 has a body portion 807 positioned between ends 802 and 804 and spaces 806 are formed between wires 801 when device 800 is dilated as shown. Spaces 806 are preferably (but not necessarily) greater between wires 801 in body portion 807 than the spaces 806 between the wires 801 at end 802 or end 803 when device 800 is dilated. A band of wires 850 may be formed near the center of body portion 807 to add greater radial strength, and the spaces between the wires 801 in such a band are typically smaller than the spaces between the wires 801 in other parts of body portion 807.

Figure 9:
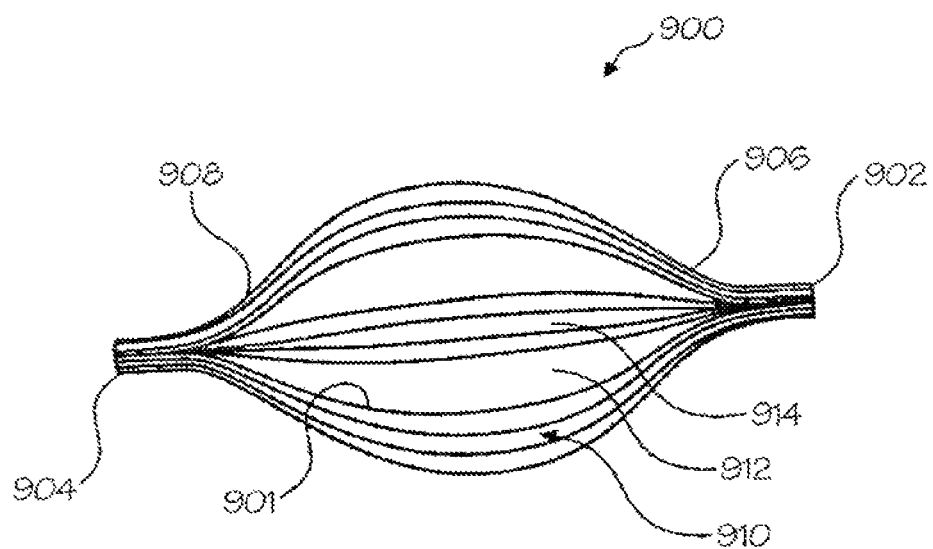
FIG. 9 shows a side view of an embodiment of a dilation device of the present disclosure in a dilated position.

FIG. 9 shows a device 900 according to the disclosure that is in the dilated position and comprises a plurality of wires 901. In this embodiment each wire 901 is parallel to the other wires 901 (in this context "parallel" means substantially parallel). Each of the wires 901 is also parallel to the vessel flow path when device 900 is inserted into a vessel (again, in this context, "parallel" means substantially parallel). Device 900 as shown is formed by slitting a tube and has unslitted ends 902, 904 a proximal end 906 and a distal end 908. Device 900 has a body portion 910 between proximal end 906 and distal end 908. As shown, wires 901 are formed in three-wire groups with distances 912 between the groups and distances 914 between wires in each group. Distances 912 are greater than distances 914 and each of the respective distances 912 and 914 are greater in body portion 910 than they are at either proximal end 906 or distal end 908.

Figure 10:
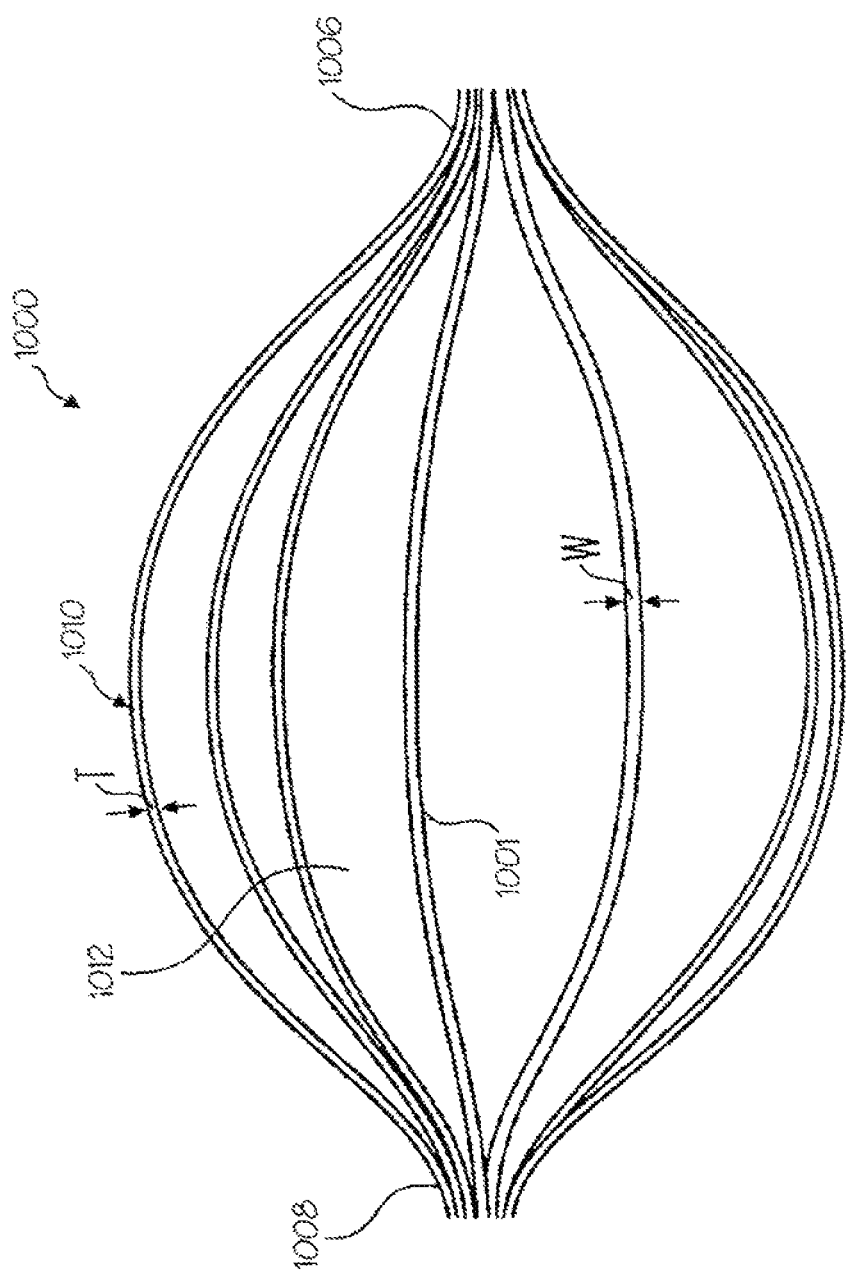
FIG. 10 shows a side view of an embodiment of a dilation device of the present disclosure in a dilated position.

FIG. 10 shows a device 1000 that is in a dilated position. Device 1000 comprises a plurality of wires 1001 and is preferably formed by slitting a tube and leaving the ends of the tube (not shown in this FIG.) unslit. In this embodiment each of the wires 1001 is parallel (in this context "parallel" means substantially parallel) to the other wires 1001 and each of the wires 1001 is also parallel (again, in this context, "parallel" means substantially parallel) to the vessel flow path when device 1000 is positioned in a vessel. Each wire 1001 is preferably a strut having a generally rectangular cross section and preferably having a width greater than its thickness. The width could be any suitable width but is preferably between 0.020" and 0.050" and the thickness could be any suitable thickness but is preferably between 0.008" and 0.018". Device 1000 has a proximal end 1006, a distal end and 1008 and a body portion 1010. There is a distance 1012 between wires 1001 and in this embodiment the distance 1012 is greater in body portion 1010 than in either proximal end 1006 or distal end 1008.

Figure 11:
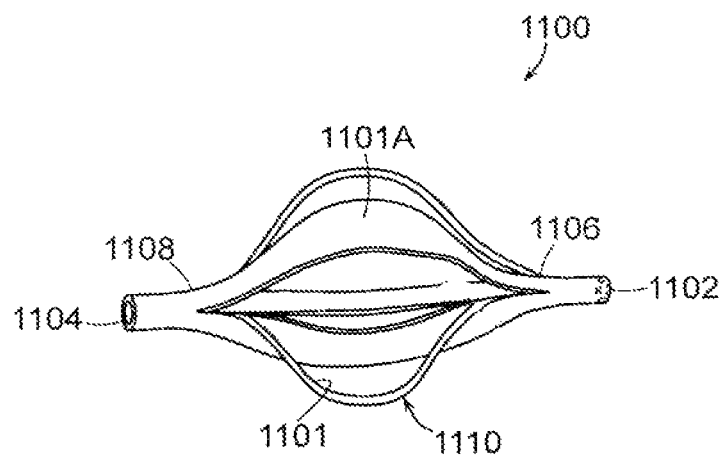
FIG. 11 shows a side view of an embodiment of a dilation device of the present disclosure in a dilated position.
Figure 12:
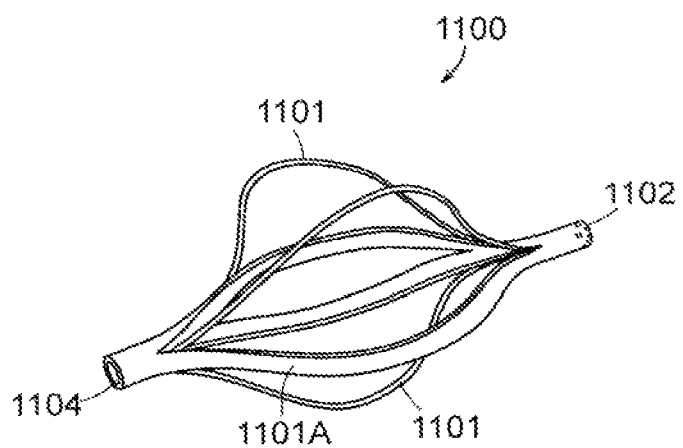
FIG. 12 is a perspective view of the dilation device of FIG. 11.

FIGS. 11 and 12 show a device 1100 according to the disclosure that is in a dilated position and that comprises a plurality of wires 1101. In this embodiment each wire 1101 is parallel to the other wires 1101 (in this context "parallel" means substantially parallel). Each of the wires 1101 are also parallel to the vessel flow path when device 1100 is inserted into a vessel (again, in this context, "parallel" means substantially parallel). Device 1100 as shown is formed by slitting a tube and has unslitted ends 1102 and 1104 (shown in FIG. 12) that are connected, respectively, to proximal end 1106 and distal end 1108. Device 1100 has a body portion 1110 between proximal end 1106 and distal end 1108. Device 1100 has two types of wires, wires 1101 and 1101A. As shown wires 1101 are slender, having a preferred width of between about 0.008" and 0.014" whereas wires 1101A are wider and have a width of between about 0.020" and 0.025." Wires 1101 also extend further from the center of body portion 1110 than do wires 1101A. In this embodiment wires 1101 and 1101A function together to apply even pressure to a substantial area of a vessel and/or apply even pressure to a substantial area of a structure to be positioned within a vessel.

Figure 13:
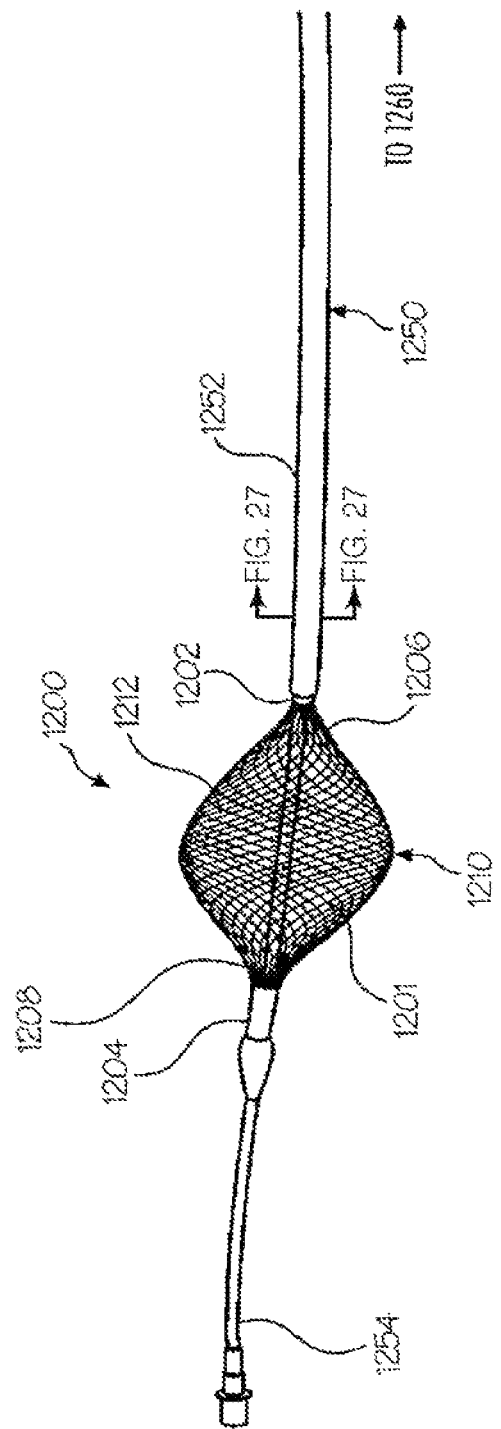
FIG. 13 shows an embodiment of a dilation device in an expanded position and a catheter of the present disclosure.

FIG. 13 shows a device 1200 according to the disclosure that is mounted on a catheter 1250. Catheter 1250 includes a catheter sheath 1252, a proximal end 1260 (best seen in FIG. 26), which is outside of the patient's body during a procedure and is juxtaposed the operator when catheter 1250 is in use, and a distal end 1254 that is inserted into the body. In an embodiment, the catheter 1250 is of a triaxial design.

Figure 27:
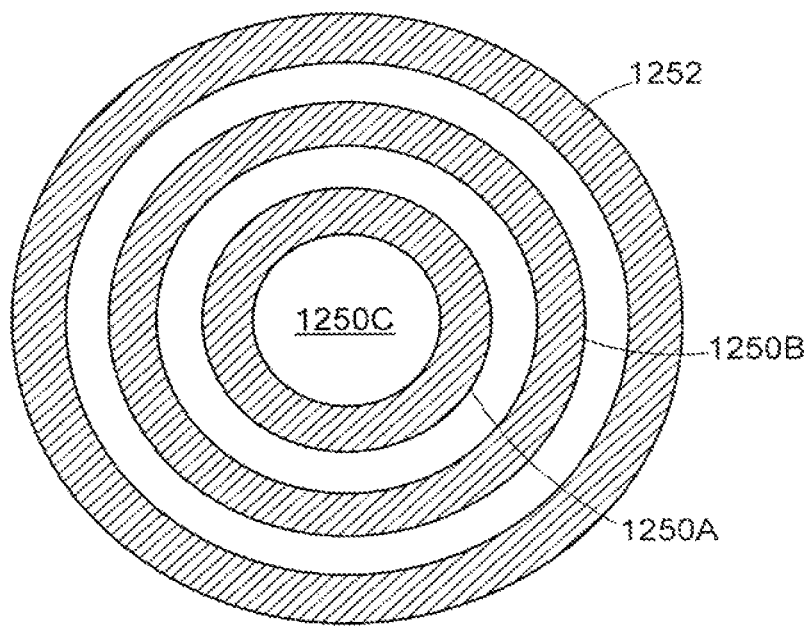
FIG. 27 is a cross-sectional view of the catheter of FIG. 13. The catheter is of a triaxial design.
Figure 30:
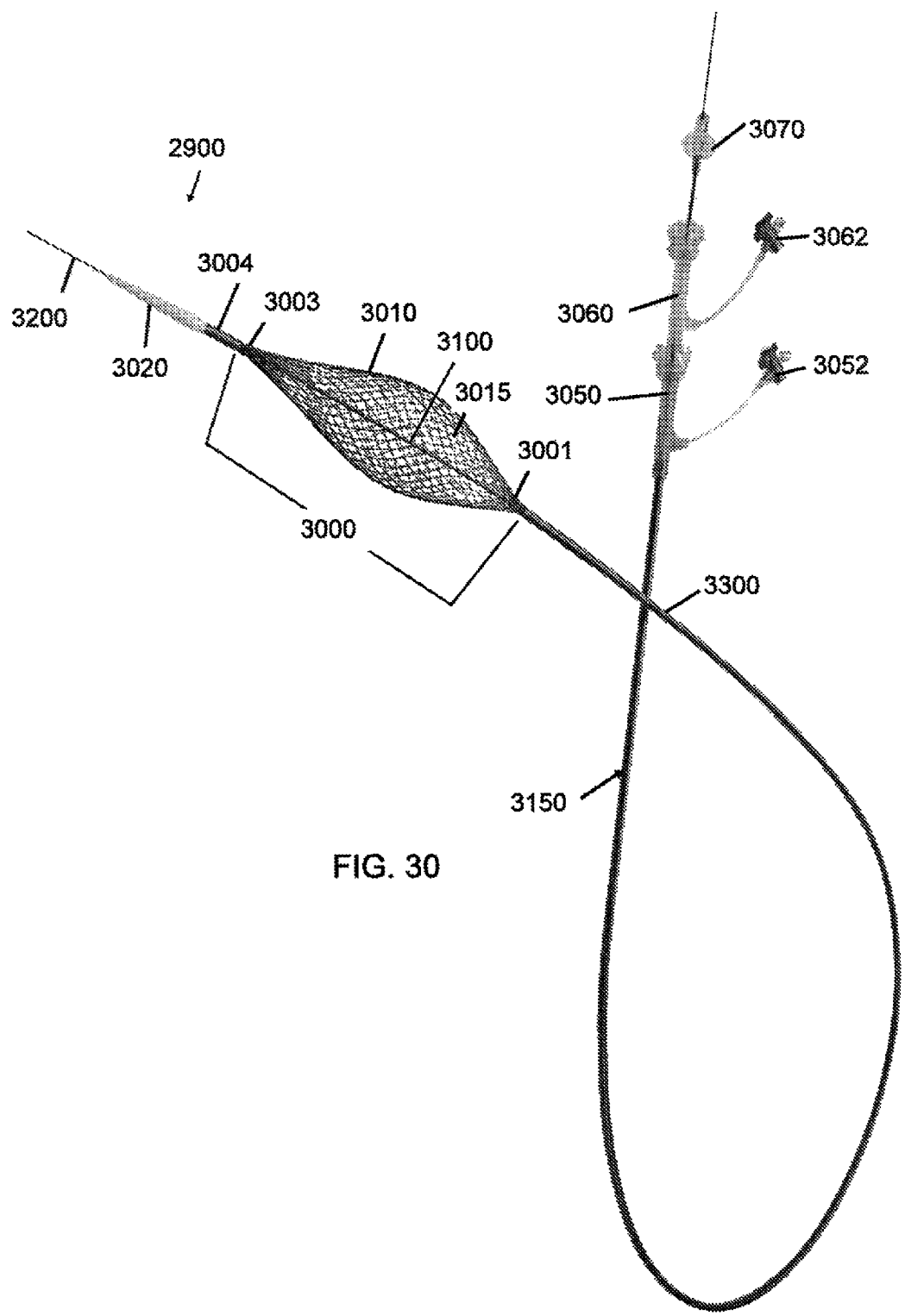
FIG. 30 shows a perspective view of an embodiment of a modeling catheter of the present disclosure including a dilation device and a catheter.
Figure 31:
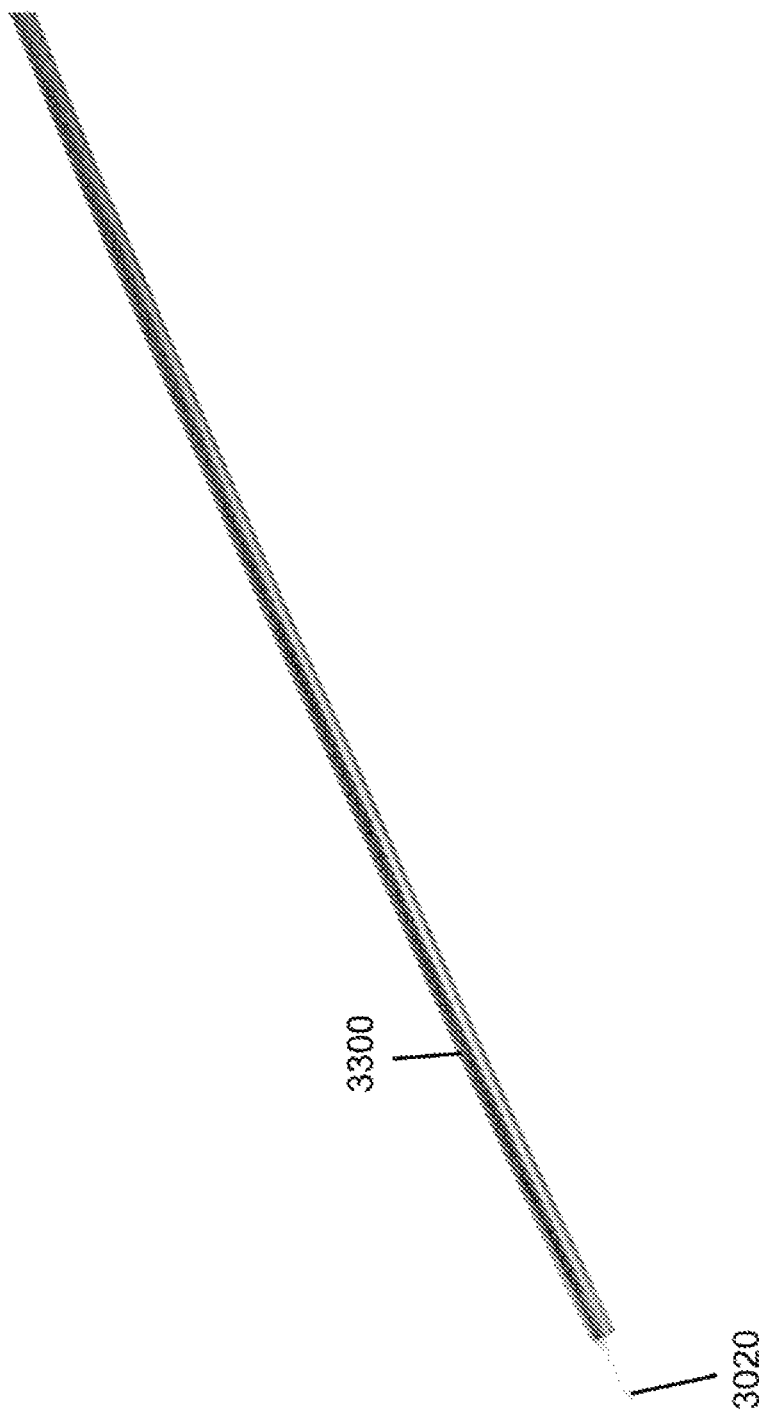
FIG. 31 shows an enlarged perspective view of a distal end of the modeling catheter of FIG. 30 with the dilation device sheathed.
Figure 32:
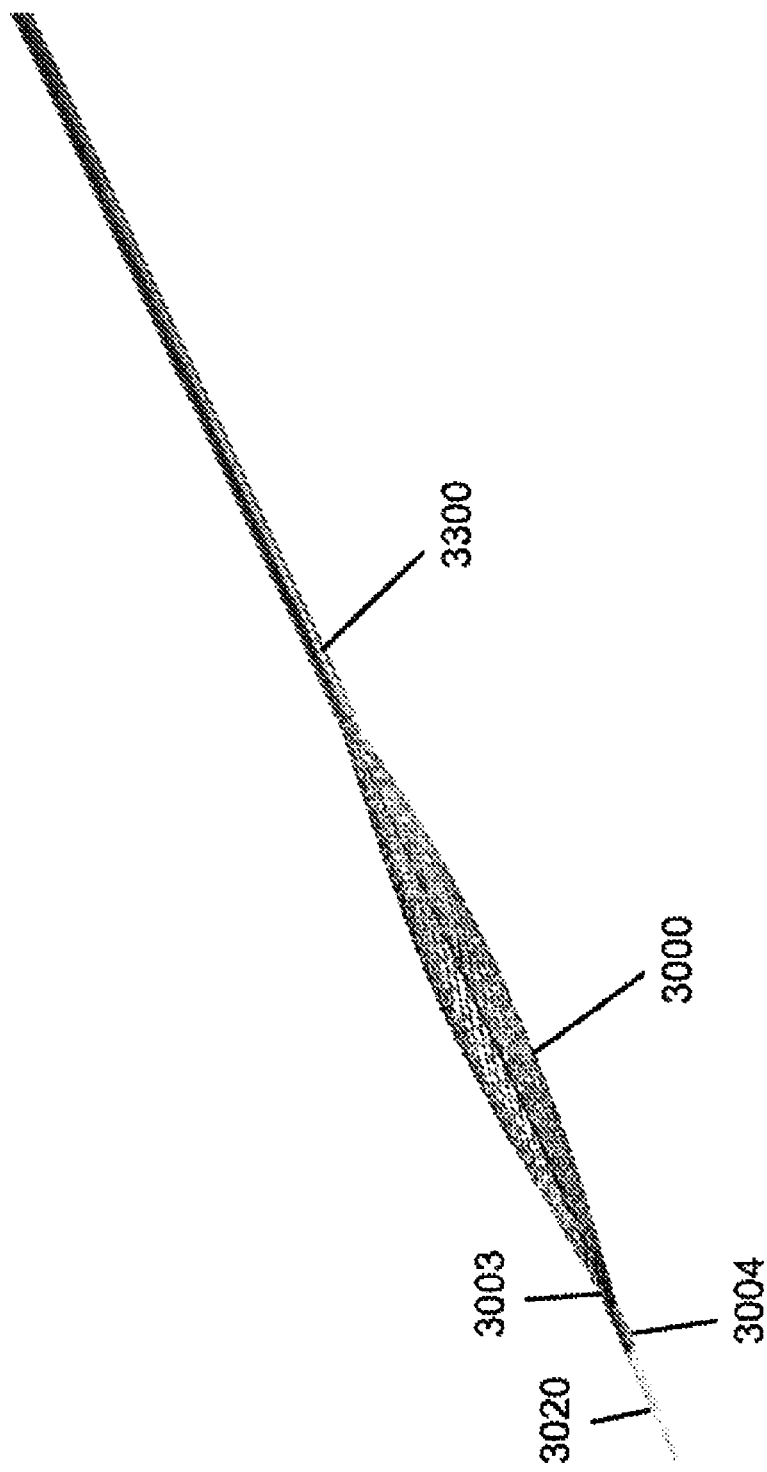
FIG. 32 shows an enlarged perspective view of a distal end of the modeling catheter of FIG. 30 with the dilation device unsheathed and in a relaxed state.
Figure 33:
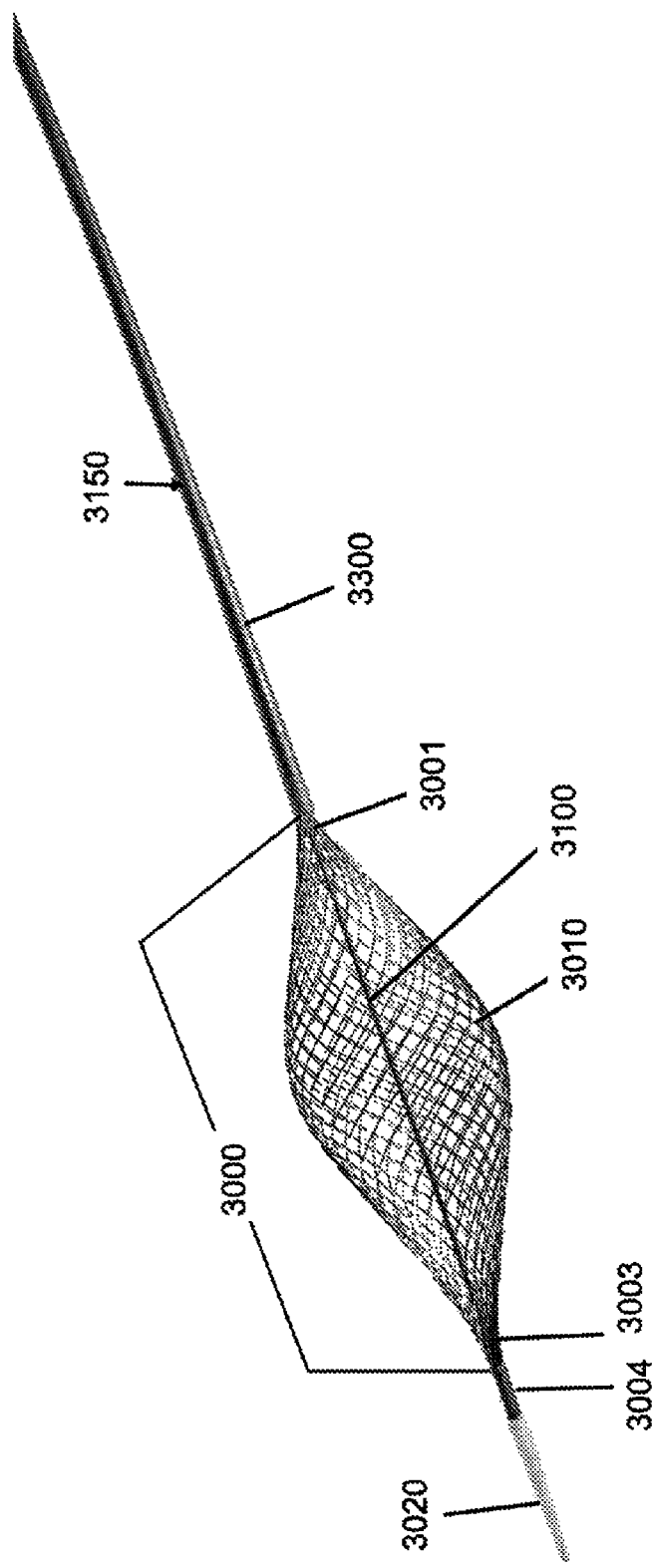
FIG. 33 shows an enlarged perspective view of a distal end of the modeling catheter of FIG. 30 in a partially dilated position.

FIG. 27 shows a cross-sectional view of catheter 1250, for example, as taken through line C-C of FIG. 13. Catheter 1250 includes, but is not limited to, three preferably coaxial tubes; central tube 1250A, outer tube 1250B and catheter sheath 1252. In this embodiment, central tube 1250A extends essentially the entire length of catheter 1250 and has a central lumen 1250C for receiving a guide wire (not shown). Central tube 1250A extends through device 1200 and is attached to device 1200 at end 1204. Outer tube 1250B is positioned over central tube 1250A and extends to end 1202 of device 1200 where the outer tube 1050B is connected to end 1202. Catheter sheath 1252 has a length sufficient to cover device 1200. Catheter 1250 may be used with any of the embodiments disclosed herein.

In operation the assembly including device 1200 and catheter 1250 is placed into a vessel with catheter sheath 1252 at least partially covering device 1200 to help retain the device 1200 in its collapsed position and to allow for ease in directing the catheter and device through the vessel.

Once device 1200 is properly positioned in a vessel, catheter sheath 1252 is pulled back to expose device 1200. Device 1200 can then be dilated by either pushing outer tube 1250B, pulling central tube 1250A or by simultaneously pushing outer tube 1250B and pulling central tube 1250A. As previously explained, the tube that is not being pushed or pulled must remain stable enough so that the distance between retention ends 1202 and 1204 decreases and device 1200 expands.

If a device according to the disclosure were being used to position a structure in the vessel, the structure (such as a stent or stent graft) could be mounted on the device in a typical manner known to those in the art so that as the device dilates the structure is dilated.

Utilizing catheter 1250 (or any suitable biaxial or triaxial catheter) a device, such as device 1200 or 1300, is dilated by moving the distal and proximal ends of the device towards each other. The device is contracted and collapsed by releasing the force pushing the two ends together and/or by moving the two ends apart.

Alternatively, any device according to the disclosure may be preformed in a dilated position and compressed into a collapsed position when covered by catheter sheath 1252. When catheter sheath 1252 is removed the preformed device would immediately expand to its dilated position and then could be contracted or further dilated by an operator utilizing the catheter in one of the manners described.

In FIG. 13, device 1200 is shown in a dilated position and comprises a plurality of wires 1201 that are formed in a criss-cross pattern. Device 1200 has retention ends 1202 and 1204 that may be formed as part of catheter 1250, a proximal end 1206, a distal end 1208 and a body portion 1210. Spaces 1212 are formed between wires 1201 and can be of any suitable size, e.g., between about 1 mm$^2$ and about 400 mm$^2$. As shown, spaces 1212 are larger in body portion 1210 than in either proximal end 1206 or distal end 1208.

Figure 14:
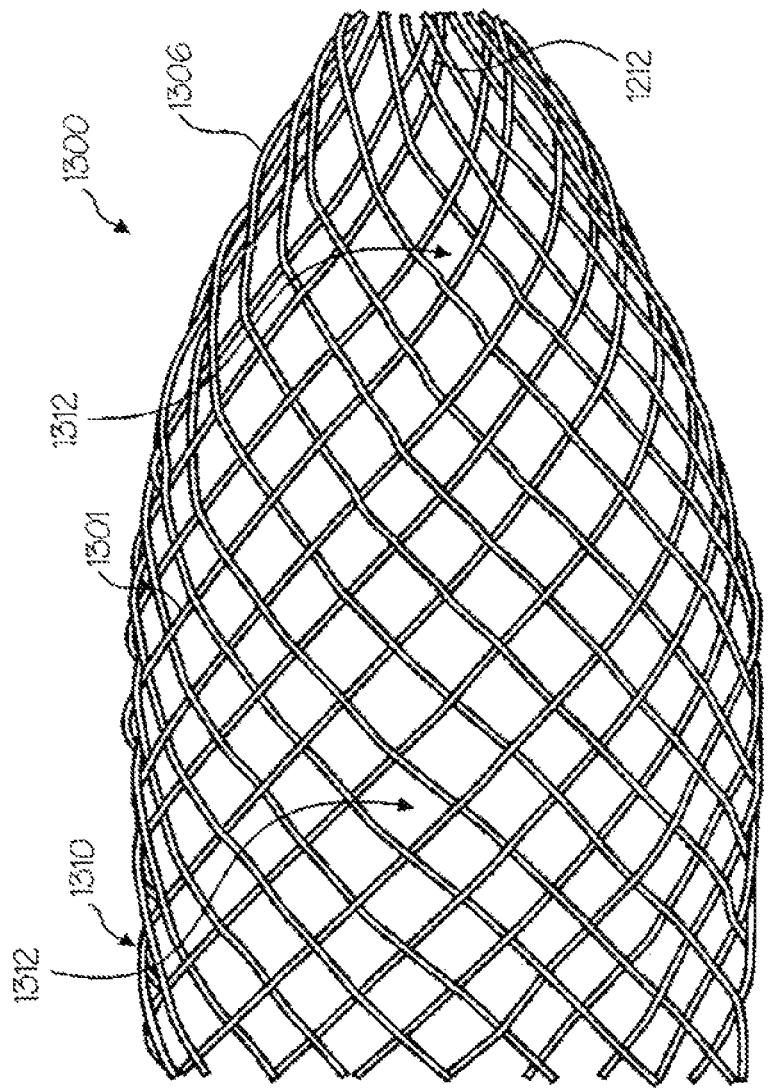
FIG. 14 is a close-up, partial side view of a dilation device of the present disclosure.

FIG. 14 is a close-up, partial side view of an alternate device 1300 showing proximal end 1306 and part of body portion 1310. As can be seen spaces 1312 between wires 1301 are smaller at proximal end 1306 than at body portion 1310.

Figure 15:
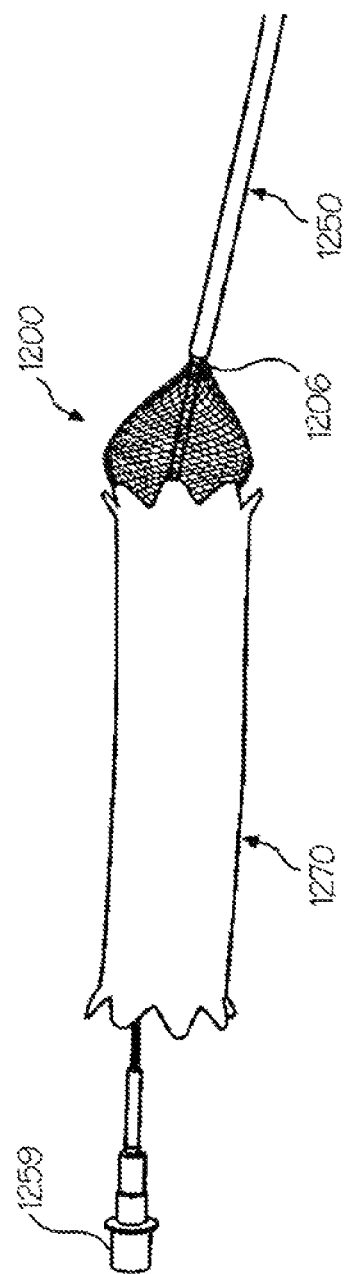
FIG. 15 shows the dilation device of FIG. 13 dilating an endoprosthesis.

FIG. 15 generally illustrates how the device 1200 can be utilized to dilate a stent graft 1270, which is shown in a dilated position. The device 1200 is positioned inside of the portion of the stent graft that will be compressed against a vessel wall to anchor the stent graft in place. As the device 1200 is expanded, the device 1200 presses the stent graft against the vessel wall.

Figure 16:
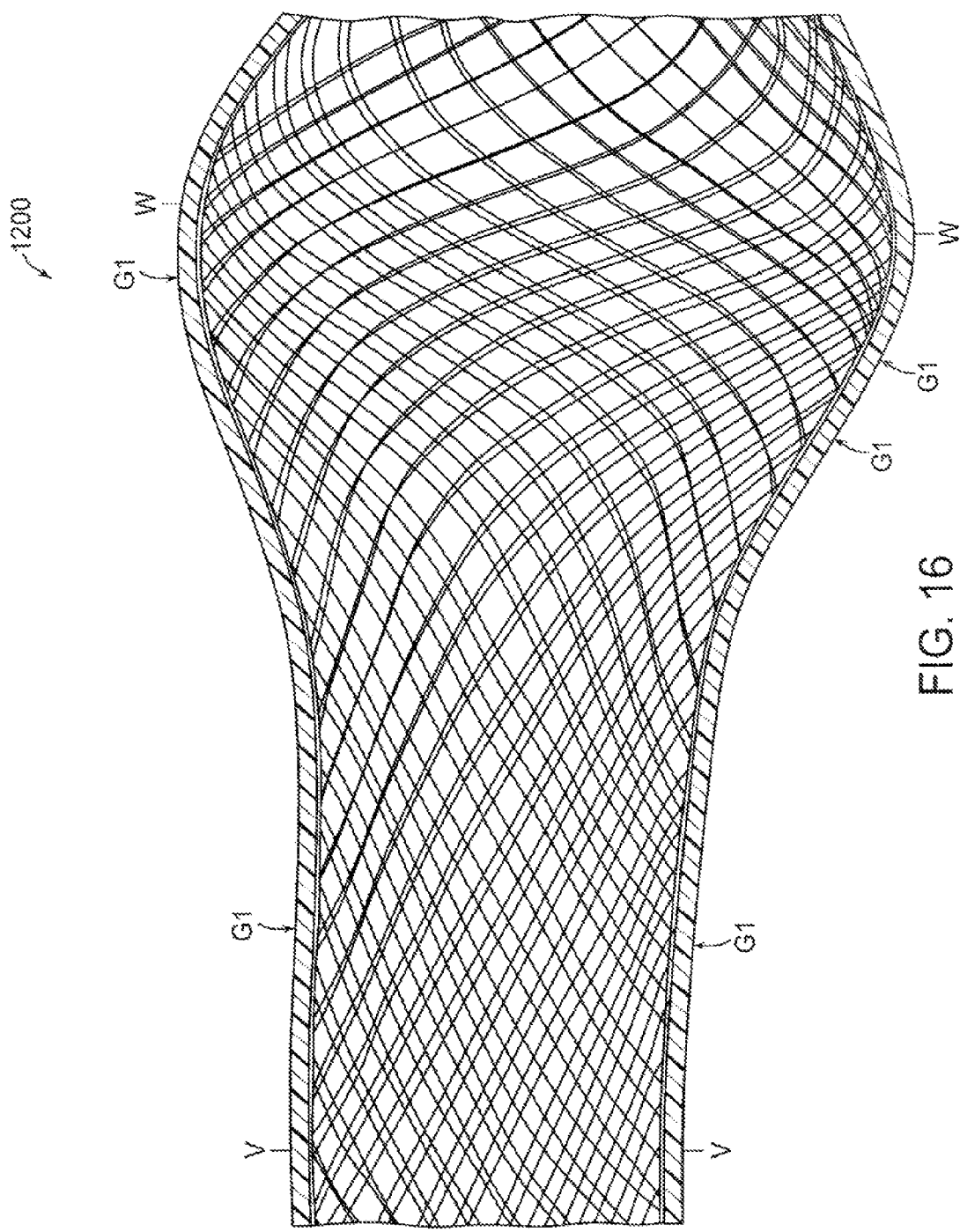
FIG. 16 shows the dilation device of FIG. 13 conforming to a diameter disparity ratio within a single vessel.

FIG. 16 shows device 1300 dilated in a plastic model G1 to simulate device 1200 conforming to a diameter disparity ratio of approximately 1.8:1 in a vessel. Device 1300 is pressed against the entire interior wall of model G1 from at least position V to a position past position W.

Figure 17:
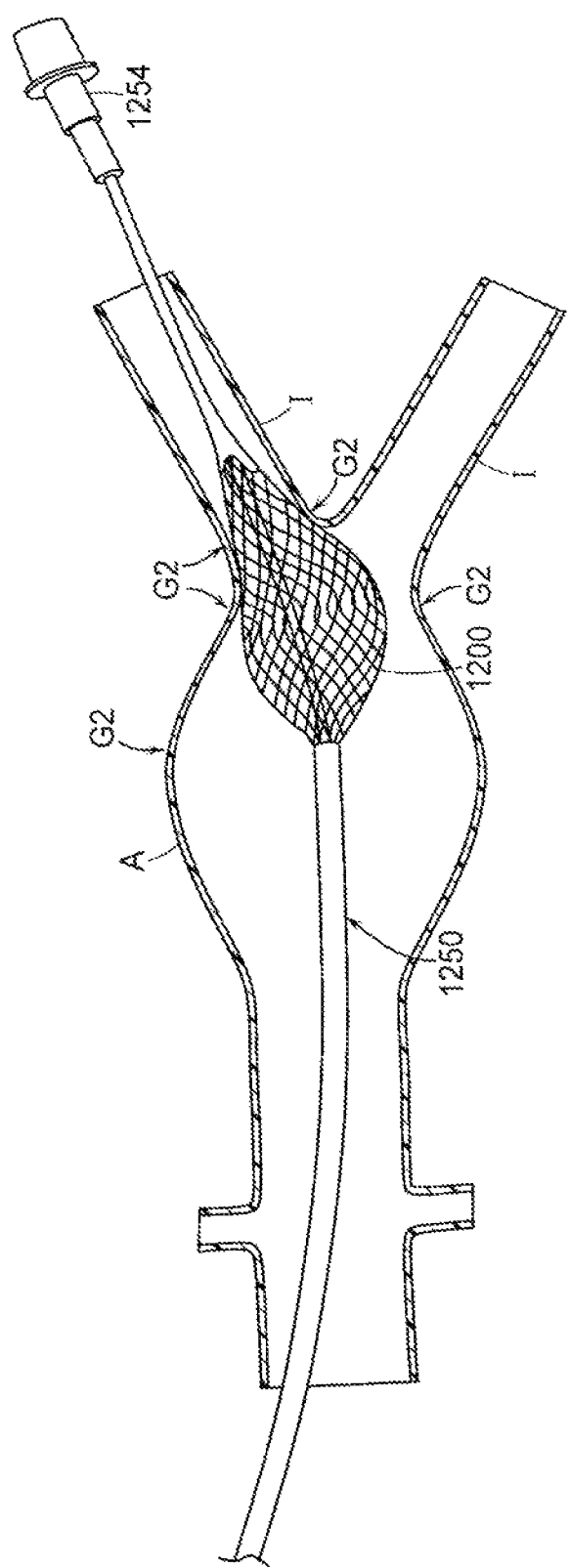
FIG. 17 shows the dilation device of FIG. 13 spanning a bifurcated vessel having different sized vessels.

FIG. 17 shows device 1200 and catheter 1270 in a plastic model G2 that simulates the aorta A and the iliac arteries I. As illustrated in FIG. 17, the device 1200 is simultaneously positioned in the aorta and an iliac artery having a multi-vessel diameter disparity ratio of about 2.0:1.

Figure 18:
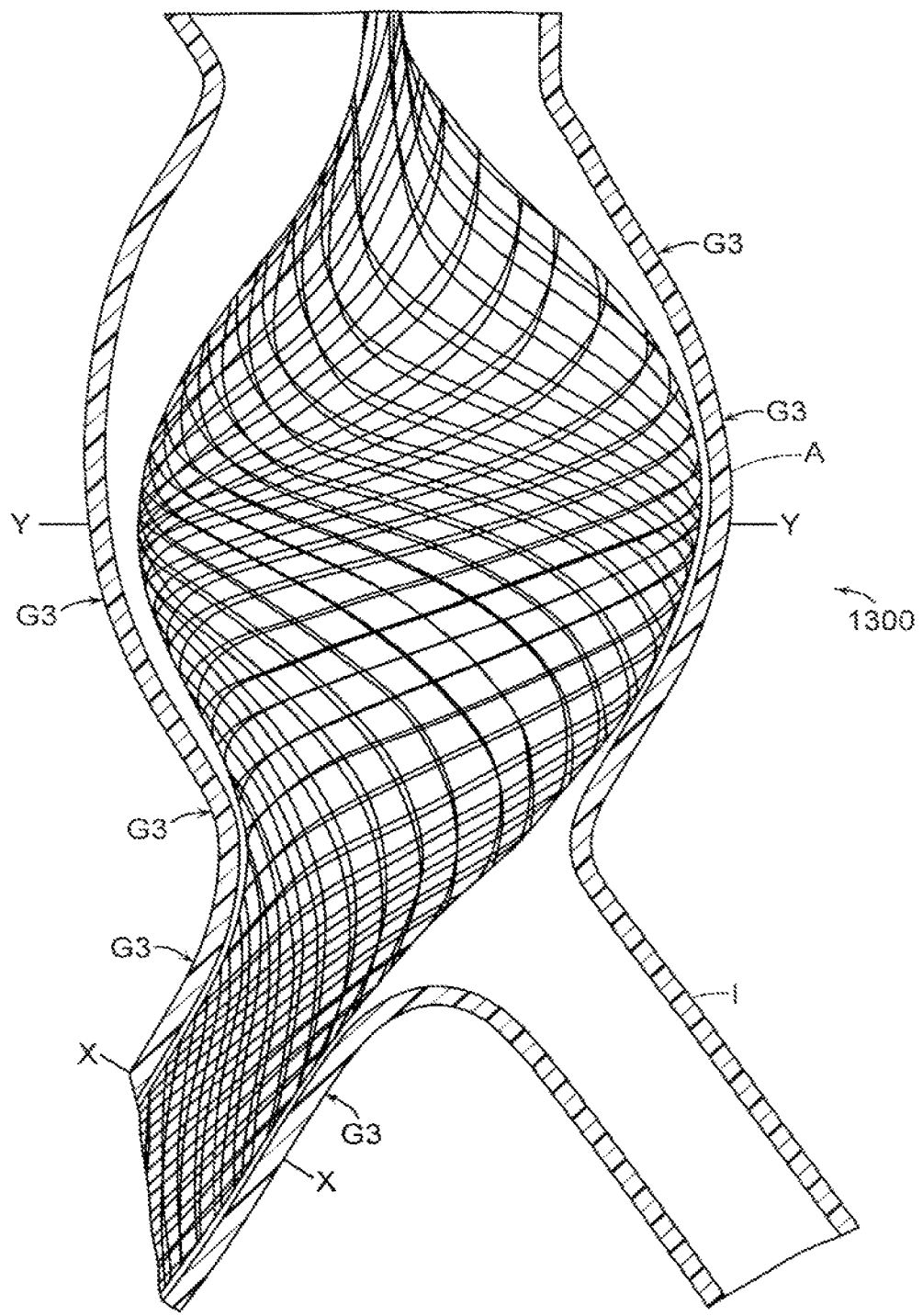
FIG. 18 shows an embodiment of a dilation device of the present disclosure conforming to a multi-vessel diameter disparity ratio within a bifurcated vessel.

FIG. 18 shows a device 1300 in accordance with the disclosure that is dilated in a plastic model G3 to simulate device 1300 being dilated simultaneously in the aorta A and an iliac artery I. As illustrated in FIG. 18, the device 1300 is positioned in multiple vessels having a multi-vessel diameter disparity ratio of about 3.4:1. In an embodiment, device 1300 is pressed against the entire interior wall of model G3 (except for one of the simulated iliac arteries I that does not include device 1300) from at least position X to a position past position Y.

Figure 19:
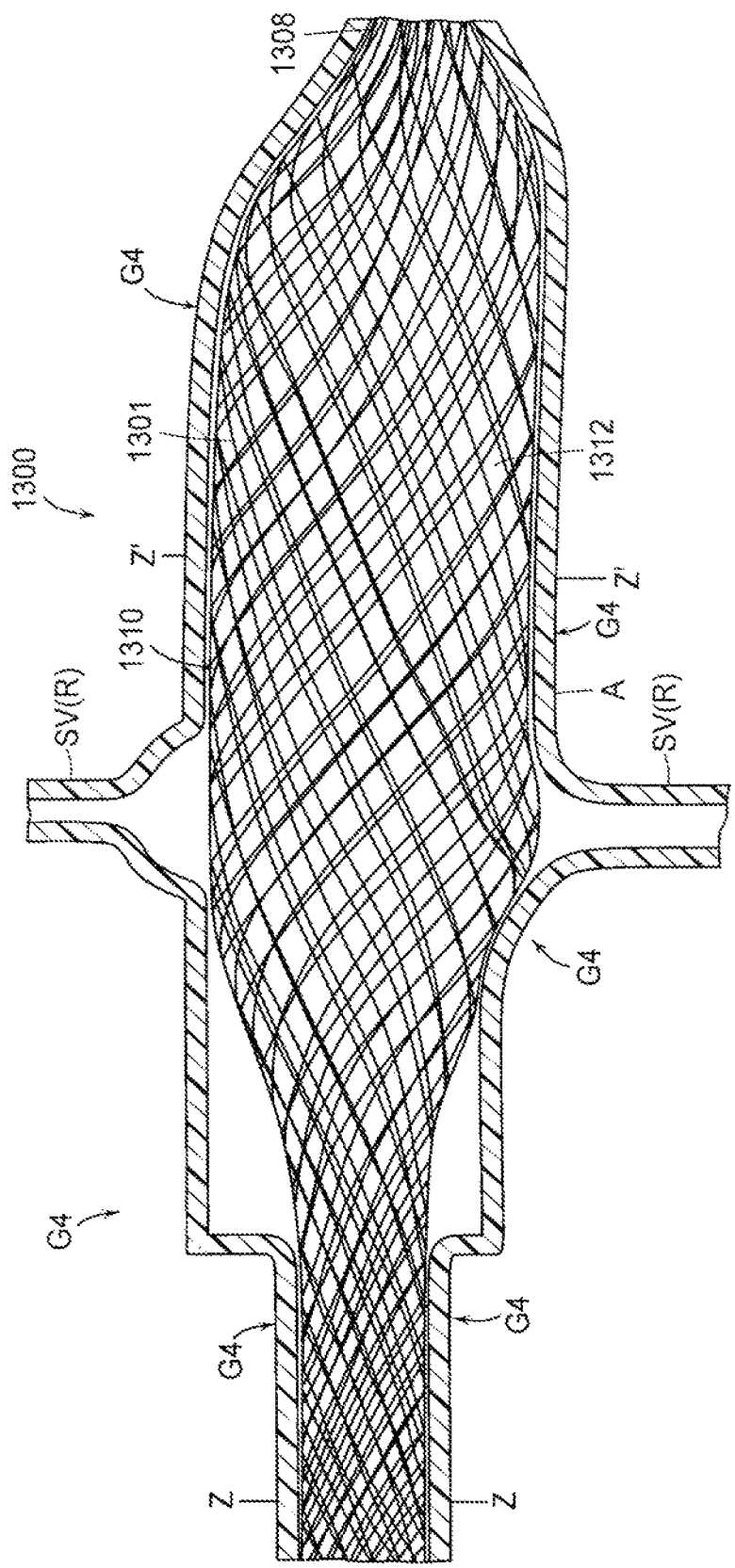
FIG. 19 shows an embodiment of a dilation device of the present disclosure conforming to a diameter disparity ratio within a single vessel.

FIG. 19 shows device 1300 with wires 1301, proximal end 1308 and spaces 1312 between wires 1301. Device 1300 is dilated in a plastic model G4 to simulate device 1300 being dilated in aorta A and covering side vessels SV(R) that simulate the renal arteries. As can be seen, fluid would flow through the spaces 1312 at proximal end 1308, through the aorta and into the side vessels through spaces 1312 in body portion 1310. In this FIG., device 1300 is also conforming to a vessel diameter disparity ratio of about 2.0:1. Device 1300 is pressed against the entire interior wall of model G4 (except for the simulated renal arteries SV (R) shown as side vessels that are covered by device 1300) from at least position Z to a position past position Z'.

Figure 20:
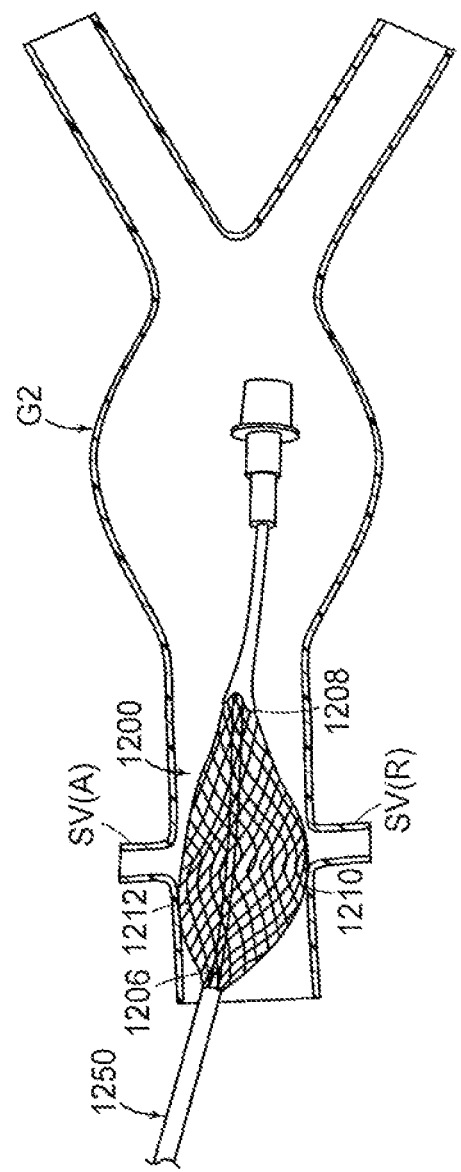
FIG. 20 shows the dilation device of FIG. 13 being positioned in an aorta and covering the renal arteries. With the dilation device expanded, the dilation device does not occlude or substantially hinder the flow of fluid to the renal arteries.

FIG. 20 shows device 1200 and catheter 1250 positioned in a plastic model G2 to simulate device 1200 being positioned and dilated in the aorta and covering side branches, such as the renal arteries SV(R). The spaces 1212 between the wires 1201 in device 1200 allow fluid to flow through the aorta and into the side vessels when device 1200 is dilated.

FIG. 21 shows the dilation device 1200 of FIG. 13 in a collapsed position and having a bend radius of about 13.5 mm. FIG. 22 shows the dilation device 1200 of FIG. 13 in a partially dilated position and having a bend radius of about 16 mm. FIG. 23 shows the dilation device 1200 of FIG. 13 in a fully dilated position and having a bend radius of about 20 mm.

In some embodiments, the dilation device may be constructed such that the kink radius is between about 0.5 inches and about 3 inches at its relaxed and/or maximum dilated diameter. The kink radius is important for use in tortuous anatomies. A dilation device of the present disclosure can have a kink radius of about 13.5 mm or greater before being dilated. This includes one or more of a kink radii of about 14.0 mm, 15.0 mm, 16.0 mm, 17.0 mm, 18.0 mm, 19.0 mm, 20.0 mm and greater. Further, a dilation device according to the present disclosure may, when fully dilated, have a kink radius of about 20.5 mm or greater. This includes one or more of the kink radii of about 21.0 mm, 22.0 mm, 23.0 mm, 24.0 mm, 25.0 mm, 26.0 mm, 27.0 mm, 28.0 mm, 29.0 mm and greater. Further, a dilation device of the present disclosure may, when fully dilated, have a kink radius of about 29.5 mm or greater. This includes one or more of a kink radii of about 30.0 mm, 31.0 mm, 32.0 mm, 33.0 mm, 34.0 mm, 35.0 mm, 36.0 mm, 37.0 mm and greater. Further, a device according to the present disclosure may, when fully dilated, have a kink radius of about 37.5 mm or greater. This includes one or more of a kink radii of 38.0 mm, 39.0 mm, 40.0 mm, 41.0 mm, 42.0 mm, 43.0 mm, 44.0 mm, 45.0 mm and greater. Further, a device according to the present disclosure may, when fully dilated, have a kink radius of about 45.5 mm or greater. This includes one or more of a kink radii of about 46.0 mm, 47.0 mm, 48.0 mm, 49.0 mm, 50.0 mm, 51.0 mm, 52.0 mm, 53.0 mm and greater.

Figure 24:
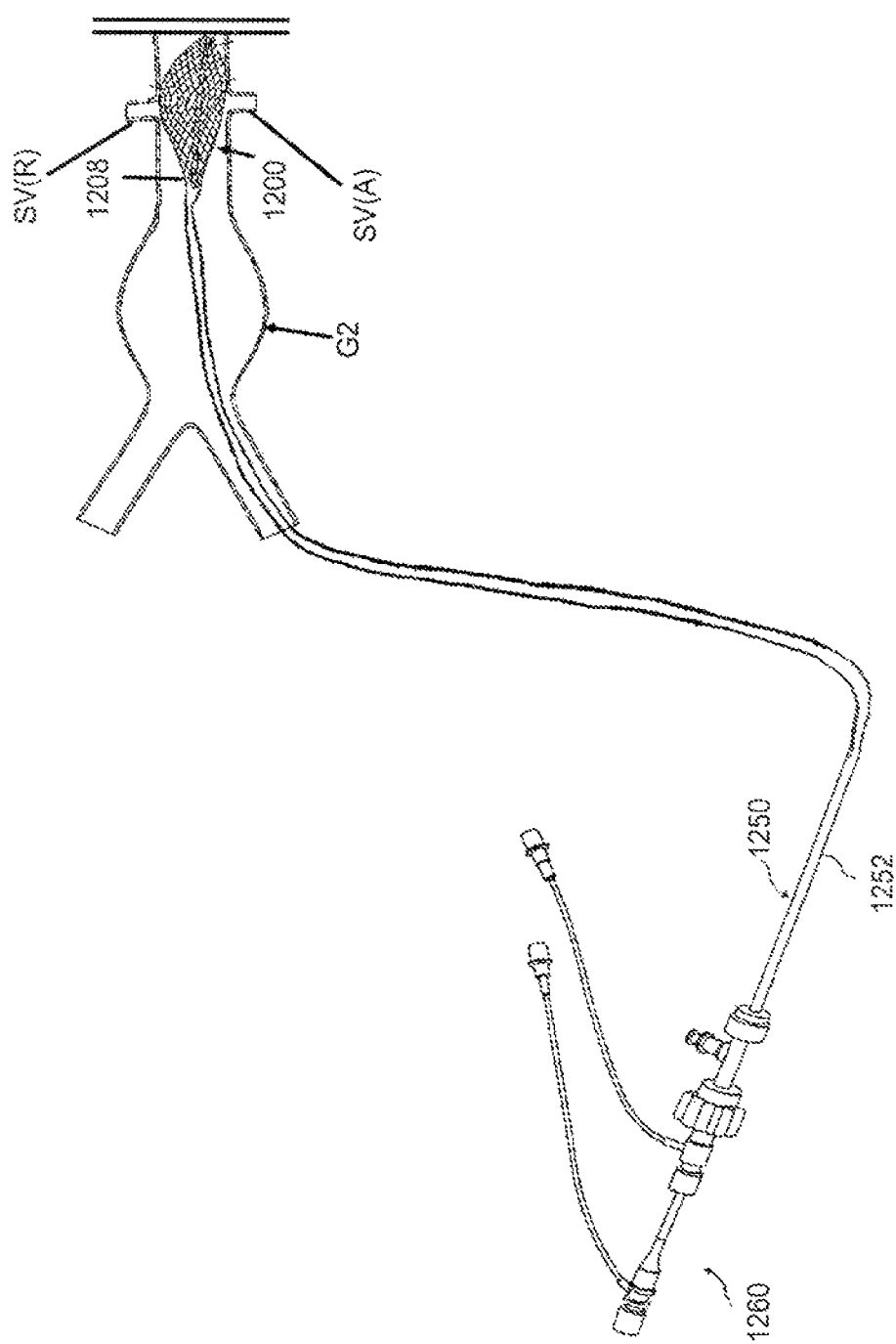
FIG. 24 is a side, perspective view of the dilation device of FIG. 13 positioned in an aorta and covering the renal arteries. With the dilation device expanded, the dilation device does not occlude or substantially hinder the flow of fluid to the renal arteries.

FIG. 24 shows the catheter 1250 of FIG. 13 having the dilation device 1200 of FIG. 13. Catheter 1250 has a proximal end 1254 that is inserted into a vessel during use, and a distal end 1260 that remains outside of the vessel and is used by an operator to position, release and dilate the dilation device 1200.

FIG. 25 is a perspective view of a distal end of the assembly of FIG. 13 with the device 1200 enclosed within the outer sheath 1252 of the catheter 1250. FIG. 26 is a perspective view of a proximal end of the assembly of FIG. 13.

FIGS. 28A-F show an embodiment of a dilation device 1400 of the present disclosure. FIGS. 28A-C show the dilation device 1400 in a first partially deflated expanded position. FIGS. 28D-F show the dilation device 1400 in a second partially deflated expanded position. The dilation device 1400 includes a proximal end 1406, a distal end 1408, and a body portion 1420 therebetween. The body portion 1420 is composed of a plurality of wires 1410. In an embodiment, the dilation device 1400 has 48 wires 1410. In an embodiment, the wires 1410 have a diameter of about 0.011 inches. In an embodiment, the proximal end 1406 and the distal end 1408 of the dilation device 1400 include radio-opaque markers or bands. The dilation device 1400 may be designed to move from a collapsed position to a partially or fully dilated, expanded position. In an embodiment, the dilation device 1400 has a collapsed diameter of about 4.20 millimeters. In an embodiment, the dilation device 1400 has a fully dilated diameter of about 55 millimeters. When the dilation device 1400 is moved to a partially of fully dilated position, spaces 1430 exist between the plurality of wires 1410. In an embodiment, these spaces 1430 range from about 0.5 mm$^2$ to about 5 mm$^2$. In an embodiment, the dilation device 1400 has a kink radius of about 50.8 mm in a relaxed state. The dilation device 1400 includes retention ends 1402 and 1404 that may engage various components of a catheter, as will be described below with relation to FIGS. 29A-C. In an embodiment, the dilation device 1400 has a length of between about 10 and about 15 centimeters. In an embodiment, the dilation device 1400 is used to dilate a single vessel having a variable diameter along a length of the vessel. In such embodiments, the dilation device 1400 may be able to conform to a diameter disparity ratio up to about 13.13:1. In an embodiment, the dilation device 1400 is used to dilate multiple vessels having different diameters. In such embodiments, the dilation device 1400 may be able to conform to a multi-vessel diameter disparity ratio up to about 5:1. In an embodiment, when the dilation device 1400 is dilated within the vessel, a pressure drop in the vessel is about zero. In an embodiment, the dilation device 1400 exerts a radial pressure as the device 1400 is dilated that ranges from about 0 to about 10.5 pounds per square inch. In an embodiment, the radial pressure is exerted over an entire working range of the dilation device 1400.

FIGS. 29A-C show a non-occlusive modeling assembly 1500 that includes the dilation device 1400 of FIG. 28A in a retractable sheath 1452. A catheter 1450 includes the retractable sheath 1452, a proximal end 1460, which is outside of a patient's body during a procedure and is juxtaposed the operator when catheter 1450 is in use, and a distal end 1454 that is inserted into the body. In the embodiment depicted in FIGS. 29A-C, the catheter 1450 is of a triaxial design. Retention end 1402 engages the distal end 1454 of the catheter 1450. A tip protector 1462 removeably engages the distal end 1454 of the catheter 1450. In an embodiment, the sheath 1452 includes at least one radio-opaque marker or radio-opaque band at a distal end. In an embodiment, the retention end 1402, and the retention end at the proximal end of the dilation device 1400 includes a radio-opaque band. The proximal end 1460 of the catheter 1450 includes a first handle 1470 having a side port 1472, a second handle 1480 having a side port 1482, and a third handle 1490 which can accommodate a guide wire. In this embodiment, the handles 1470 and 1472 are snapped together, creating a haemostatic seal. The side ports 1472 and 1482 may be used to flush the assembly 1500 with fluid, for example, sterile saline. The handles 1470, 1480 and 1490 can be advanced and retracted as necessary during a procedure for a given result. For example, the handle 1470 can be advanced while maintaining the position of the handles 1480 and 1490 to move the sheath 1452 over the dilation device 1400. The handle 1470 can be retracted while maintaining the position of the handles 1480 and 1490 to move the sheath 1452 to expose the dilation device 1400. In an embodiment, advancing both the handles 1470 and 1480 simultaneously causes the dilation device 1400 to expand during a procedure. In an embodiment, retracting the connector 1470 causes the dilation device 1400 to expand during a procedure. In an embodiment, retracting both the connector 1470 and the connector 1480 simultaneously causes the dilation device 1400 to close. The handle 1490 at the proximal end 1460 of the assembly 1500 accommodates a guide wire.

FIGS. 30-33 show an embodiment of a non-occlusive modeling catheter 2900 of the present disclosure. The modeling catheter 2900 includes a dilation device 3000 mounted on a catheter 3150. In an embodiment, the dilation device 3000 is a nitinol mesh. The dilation device 3000 has a plurality of compliant wires 3010 braided in an overlapping pattern and having a length spanning between a proximal end 3001 and a distal end 3003. The catheter 3150 is of a triaxial design and includes a central tube 3100, an outer tube (not visible) and a sheath 3300. The central tube 3100 extends essentially the entire length of catheter 3150 and has a central lumen for receiving a guide wire 3200. The central tube 3100 has a proximal portion, a distal portion, and a central portion extending through the device 3000. The central tube 3100 is attached to the device 3000 at end 3020 An outer tube (not visible) is positioned coaxially around the proximal portion of the central tube 3100 and extends to proximal retention radio-opaque marker band (not visible) of the device 3000 where the outer tube is connected. The proximal retention radio-opaque marker band also engages the proximal end 3001 of the device 3000. A distal retention radio-opaque marker band 3004 engages the central tube 3100 at a first end and engages the distal end 3003 of the device 3000 at a second end. The retractable sheath 3300 is positioned coaxially around the outer tube and slidably moveable over the device 3000 to collapse the device 3000, relax the device 3000, and dilate the device 3000. The sheath 3300 has a length sufficient to cover device 3000. In an embodiment, the sheath 3300 is a 14 French retractable sheath. Catheter 3150 may be used with any of the dilation devices disclosed herein. In an embodiment, the retractable sheath 3300 includes at least one radio-opaque marker or band near end 3302.

In an embodiment, the number of wires 3010 used to make the braid of the device 3000 is 48. In an embodiment, the wires 3010 have a diameter of about 0.011 inches. In an embodiment, the proximal end 3001 and the distal end 3003 of the dilation 3000 include radio-opaque markers or bands. The dilation device 3000 may be designed to move from a collapsed position to a partially or fully dilated, expanded position. In an embodiment, the dilation device 3000 has a collapsed diameter of about 4.2 millimeters. In an embodiment, the dilation device 3000 has a relaxed diameter of about 25 millimeters. In an embodiment, the dilation device 3000 has a fully dilated diameter of about 55 millimeters. The dilation device 3000 includes a plurality of spaces 3015 between the plurality of wires 3010. In an embodiment, these spaces 3015 range from about 0.5 mm$^2$ to about 5 mm$^2$. In an embodiment, the dilation device 3000 has a kink radius of about 50.8 mm in a relaxed state. In an embodiment, the dilation device 3000 has a length of between about 10 and about 15 centimeters. In an embodiment, the dilation device 3000 is used to model an endoprosthesis positioned in a single vessel having a substantially constant diameter along a length of the vessel. In an embodiment, the dilation device 3000 is used to model an endoprosthesis positioned in a single vessel having a variable diameter along a length of the vessel. In such embodiments, the dilation device 3000 may be able to conform to a diameter disparity ratio ranging from about 1:1 to about 10:1. In an embodiment, the dilation device 3000 is used to model an endoprosthesis positioned in a single vessel that is substantially straight. In an embodiment, the dilation device 3000 is used to model an endoprosthesis positioned in a single vessel that has a bend. In an embodiment, the dilation device 3000 is used to model an endoprosthesis positioned in a bifurcated vessel having different diameters. In such embodiments, the dilation device 3000 may be able to conform to a multi-vessel diameter disparity ratio ranging from about 2:1 to 20:1. In an embodiment, when the dilation device 3000 is dilated within the vessel, a pressure drop in the vessel is about zero. In an embodiment, the dilation device 3000 exerts a radial pressure or force on an endoprosthesis as the device 3000 is dilated that ranges from about 0 to about 10.5 pounds per square inch. In an embodiment, the radial pressure is exerted over an entire working range of the dilation device 3000. In an embodiment, the radial pressure is substantially the same over an entire working range of the dilation device 3000.

In an embodiment, the modeling catheter 2900 includes a proximal end having a first handle 3050 having a side port 3052, and a second handle 3060 having a side port 3062. In an embodiment, the two handles 3050 and 3060 may snap together, creating a haemostatic seal. In an embodiment, the two handles 3050 and 3060 may screw together, creating a haemostatic seal. In an embodiment, the two handles 3050 and 3060 may not interact yet create a haemostatic seal. The side ports may be used to flush the assembly 2900 with fluid, for example, sterile saline. The handles can be advanced and retracted as necessary during a procedure for a given result. For example, the first handle 3050 can be advanced while maintaining the position of the second handle 3060 to move the sheath 3300 over the dilation device 3000. The first handle 3050 can be retracted while maintaining the position of the second handle 3060 to move the sheath 3300 to expose the dilation device 3000. In an embodiment, advancing both the handles simultaneously causes the dilation device 3000 to expand during a procedure. In an embodiment, the handle 3070 can be retracted while maintaining the position of the first handle 3050 and the second handle 3060 to expand the dilation device 3000. In an embodiment, a user of the catheter 2900 can optimize the radial force exerted on an endoprosthesis by manual control of the handles. Retracting the handles simultaneously causes the dilation device 3000 to close.

In an embodiment, there may be a stop built into any one of the catheters of the present disclosure to prevent the dilation device from over expanding. In an embodiment, there may not be a stop to prevent the dilation device from over expanding. In an embodiment, the stop may be incorporated in the proximal handles. In an embodiment, the stop may be in the distal tip. In an embodiment, the stop may be inside the dilation device. In an embodiment, the stop may be created to allow a range of fully expanded diameters between about 10 mm and about 55 mm.

In an embodiment, there may be multiple radio-opaque marker bands to assist with locating the dilation device, the center of the dilation device, or the ends of the dilation device. In an embodiment, there may be a single radio-opaque marker band to assist with locating the dilation device, the center of the dilation device, or the ends of the dilation device. In an embodiment, during use, the modeling catheter is positioned so that the intended modeling zone is between the two radio-opaque marker bands on the device.

In an embodiment, the dilation device 3000 has 48 round solid nitinol wires 3010 having a braided configuration, wherein each of the wires 3010 has a diameter of about 0.28 mm, a length of about 15 cm, a braid density of about 7 ppi, and a space 3015 between wires 3010 of about 3 mm$^2$. In an embodiment, the dilation device 3000 has a fully expanded outer diameter of about 55 mm, a collapsed diameter of about 4.7 mm, and a relaxed diameter of about 25 mm. The dilation device 3000 can be used with a vessel having a diameter disparity ratio of 10:1. In an embodiment, a kink radius of the dilation device 3000 is about 2 inches (~51 mm) in a relaxed state. In an embodiment, a kink radius of the dilation device 3000 is about 2 inches (~51 mm) in a dilated state.

The wires 3010 used in the dilation device 3000 may be of any suitable size, shape, thickness and material. The dilation device may 3000 include wires 3010 arranged in any suitable pattern such as a braid pattern. In the embodiment depicted in FIGS. 30-33, the wires 3010 are braided in an overlapping pattern.

In an embodiment, a device of the present disclosure includes a plurality of compliant wires braided in a double overlapping pattern and having a length spanning between a proximal end of the device and a distal end of the device, wherein the device is positioned in at least a portion of an endoprosthesis implanted in a single vessel, wherein, when the device is in a relaxed state, a plurality of spaces are formed between the plurality of wires to allow fluid to move freely through the plurality of spaces, wherein, when the device is in a dilated state, the plurality of wires are sufficiently designed to exert a radial force on the endoprosthesis while continually allowing the fluid to move freely through the plurality of spaces, and wherein, when the device is in the dilated state, the plurality of wires are sufficiently designed to conform to a diameter disparity ratio in the single vessel ranging from about 1:1 to about 10:1. In an embodiment, the device is positioned in the endoprosthesis to enhance primary attachment of the endoprosthesis to the single vessel. In an embodiment, the device is positioned in the endoprosthesis to repair a collapse in the endoprosthesis. In an embodiment, the device is positioned in the endoprosthesis to repair infolding of the endoprosthesis. In an embodiment, the device is positioned in the endoprosthesis to repair an endoleak in the endoprosthesis.

In an embodiment, a device of the present disclosure includes a plurality of compliant wires braided in a double overlapping pattern and having a length spanning between a proximal end of the device and a distal end of the device, wherein the device is sufficiently designed to expand from a relaxed state to a dilated state, wherein the device is positioned in at least a portion of an endoprosthesis implanted in a bifurcated vessel, wherein, when the device is in the relaxed state, the overlapping pattern creates a plurality of spaces between the plurality of wires allowing fluid to move freely through the plurality of spaces, wherein, when the device is in the dilated state, the plurality of wires are sufficiently designed to exert a radial force on the endoprosthesis while continually allowing the fluid to move freely through the plurality of spaces, and wherein, when the device is in the dilated state, the plurality of wires are sufficiently designed to conform to a multi-vessel diameter disparity ratio in the bifurcated vessel ranging from about 2:1 to 20:1. In an embodiment, the device is positioned in the endoprosthesis to enhance primary attachment of the endoprosthesis to the single vessel. In an embodiment, the device is positioned in the endoprosthesis to repair a collapse in the endoprosthesis. In an embodiment, the device is positioned in the endoprosthesis to repair infolding of the endoprosthesis. In an embodiment, the device is positioned in the endoprosthesis to repair an endoleak in the endoprosthesis.

In an embodiment, a method of assisting in modeling of a self expanding endoprosthesis in a vessel includes providing a non-occlusive modeling assembly comprising a catheter having at a distal end a dilation device sufficiently designed to expand and collapse, and at a proximal end at least two connectors moveable along a length of the catheter; and a retractable sheath positioned coaxially around the catheter and moveable along a length of the catheter to cover and expose the dilation device, wherein the dilation device and the sheath include at least one radio-opaque marker; positioning the dilation device inside the endoprosthesis residing within the vessel; and expanding the dilation device by advancing the two connectors simultaneously, or retracting the most proximal connector, until a desired modeling is exerted on the endoprosthesis. In an embodiment, the method is performed under fluoroscopy.

In an embodiment, the assembly is flushed with sterile saline via ports on the two connectors until fluid exits a distal end of the sheath. In an embodiment, about 20 to about 30 cc of saline are used to flush the assembly prior to use. In an embodiment, the dilation device is positioned inside the endoprosthesis in a "sheathed position". A sheathed position refers to the dilation device being entirely surrounded by the sheath of the assembly. This can be accomplished by maintaining one of the connectors (the most proximal connector) in a stationary position, and advancing the other connector (the most distal connector) towards the distal end of the assembly or retracting the most proximal connector. Once the dilation device is properly positioned inside the endoprosthesis, the dilation device is "unsheathed". This can be accomplished by maintaining one of the connectors (the most proximal connector) in a stationary position, and retracting the other connector (the most distal connector) towards the proximal end of the assembly The dilation device can then be expanded within the endoprosthesis by simultaneously advancing both connectors towards the distal end of the assembly. Proper modeling should show slight expansion of the endoprosthesis. To close the dilation device, both of the connectors are simultaneously retracted towards the proximal end of the assembly. The sheathing and unsheathing steps can be performed as many times as needed for proper modeling. In an embodiment, the dilation device should not be expanded more than 20 times for a procedure.

In an embodiment, a method of modeling an endoprosthesis includes gaining access to an endoprosthesis positioned in a vessel; guiding a dilation device of the present disclosure into position within the endoprosthesis using a guide wire so that an intended modeling zone is between two radio-opaque marker bands located on the dilation device, wherein the dilation device is fully sheathed during positioning; unsheathing the dilation device in the endoprosthesis; expanding the dilation device to model the endoprosthesis to a wall of the vessel, wherein the dilation device is expanded until a desired amount of radial force is exerted on the endoprosthesis; collapsing the dilation device; resheathing the dilation device fully; and removing the dilation device from the endoprosthesis. In an embodiment, the expansion and the collapsing of the dilation device is repeated as necessary to model the endoprosthesis to the wall of the vessel. In an embodiment, the method further includes confirming that the endoprosthesis has not moved in the vessel. In an embodiment, the endoprosthesis is positioned in a single vessel. In an embodiment, the single vessel has a straight length. In an embodiment, the single vessel has a bend. In an embodiment, the single vessel has a diameter disparity ratio in the modeling zone. In an embodiment, the endoprosthesis is positioned in a bifurcated vessel. In an embodiment, the bifurcated vessel has a multi-vessel diameter disparity ratio in the modeling zone.

Other embodiments of the disclosure will be apparent to those skilled in the art from consideration of the specification and embodiments disclosed herein. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by this disclosure.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A device comprising:
48 round nitinol wires braided in a double overlapping pattern, wherein each of the wires has a diameter of about 0.28 mm and a length between about 10 cm and about 15 cm spanning between a proximal end of the device and a distal end of the device, wherein a braid density of the wires is about 7 ppi,
wherein the device is sufficiently designed to be positioned in at least a portion of an endoprosthesis implanted in a single vessel,
wherein, when the device is in a relaxed state and positioned in the endoprosthesis, a plurality of spaces are formed between the plurality of wires to allow fluid to move freely through the plurality of spaces,
wherein, when the device is in a dilated state and positioned in the endoprosthesis, the plurality of wires are sufficiently designed to exert a radial force on the endoprosthesis while continually allowing the fluid to move freely through the plurality of spaces, and
wherein, when the device is in the dilated state and positioned in the endoprosthesis, the plurality of wires are sufficiently designed to conform to a diameter disparity ratio in the single vessel ranging from about 1:1 to about 10:1.

2. The device of claim 1 wherein, when the device is positioned in the endoprosthesis, the device is sufficiently designed to enhance primary attachment of the endoprosthesis to the single vessel.

3. The device of claim 1 wherein, when the device is positioned in the endoprosthesis, the device is sufficiently designed to repair a collapse in the endoprosthesis.

4. The device of claim 1 wherein, when the device is positioned in the endoprosthesis, the device is sufficiently designed to repair infolding of the endoprosthesis.

5. The device of claim 1 wherein, when the device is positioned in the endoprosthesis, the device is sufficiently designed to repair an endoleak in the endoprosthesis.

6. The device of claim 1 wherein the plurality of spaces formed between the plurality of wires range from about 0.5 $mm^2$ to about 5 $mm^2$.

7. The device of claim 1 wherein, when the device is in the dilated state and positioned in the endoprosthesis, the radial force exerted on the endoprosthesis by the plurality of wires ranges from about 0 psi to about 20 psi.

8. The device of claim 1 wherein, when the device is in the relaxed state and positioned in the endoprosthesis, at least a portion of the device has a diameter ranging from about 5 mm to about 30 mm.

9. The device of claim 1 wherein, when the device is in the dilated state and positioned in the endoprosthesis, at least a portion of the device has a diameter ranging from about 10 mm to about 70 mm.

10. The device of claim 1 wherein, when the device is positioned in the endoprosthesis, the single vessel having the implanted endoprosthesis is substantially straight.

11. The device of claim 1 wherein, when the device is positioned in the endoprosthesis, the single vessel having the implanted endoprosthesis has a bend.

12. The device of claim 11 wherein, when the device is in the relaxed state and positioned in the endoprosthesis, the plurality of wires are sufficiently designed to conform to a curvature in the single vessel so that a bend radius of the device ranges from about 10 mm to about 130 mm.

13. The device of claim 11 wherein, when the device is in the dilated state and positioned in the endoprosthesis, the radial force exerted on the endoprosthesis by the plurality of wires at an inner curvature of the bend and an outer curvature of the bend is approximately equal and ranges from about 0 psi to about 20 psi.

14. A device comprising:
   48 round nitinol wires braided in a double overlapping pattern, wherein each of the wires has a diameter of about 0.28 mm and a length between about 10 cm and about 15 cm spanning between a proximal end of the device and a distal end of the device, wherein a braid density of the wires is about 7 ppi,
wherein the device is sufficiently designed to expand from a relaxed state to a dilated state,
wherein the device is sufficiently designed to be positioned in at least a portion of an endoprosthesis implanted in a bifurcated vessel,
wherein, when the device is in the relaxed state and positioned in the endoprosthesis, the overlapping pattern creates a plurality of spaces between the plurality of wires allowing fluid to move freely through the plurality of spaces,
wherein, when the device is in the dilated state and positioned in the endoprosthesis, the plurality of wires are sufficiently designed to exert a radial force on the endoprosthesis while continually allowing the fluid to move freely through the plurality of spaces, and
wherein, when the device is in the dilated state and positioned in the endoprosthesis, the plurality of wires are sufficiently designed to conform to a multi-vessel diameter disparity ratio in the bifurcated vessel ranging from about 1:1 to 20:1.

15. The device of claim 14 wherein, when the device is positioned in the endoprosthesis, the device is sufficiently designed to enhance primary attachment of the endoprosthesis to the single vessel.

16. The device of claim 14 wherein, when the device is positioned in the endoprosthesis, the device is sufficiently designed to repair a collapse in the endoprosthesis.

17. The device of claim 14 wherein, when the device is positioned in the endoprosthesis, the device is sufficiently designed to repair infolding of the endoprosthesis.

18. The device of claim 14 wherein, when the device is positioned in the endoprosthesis, the device is sufficiently designed to repair an endoleak in the endoprosthesis.

19. The device of claim 14 wherein the plurality of spaces formed between the plurality of wires range from about 0.5 $mm^2$ to about 5 $mm^2$.

20. The device of claim 14 wherein, when the device is in the dilated state and positioned in the endoprosthesis, the radial force exerted on the endoprosthesis by the plurality of wires ranges from about 0 psi to about 20 psi.

21. The device of claim 14 wherein, when the device is in the relaxed state and positioned in the endoprosthesis, at least a portion of the device has a diameter ranging from about 5 mm to about 30 mm.

22. The device of claim 14 wherein, when the device is in the dilated state and positioned in the endoprosthesis, at least a portion of the device has a diameter ranging from about 10 mm to about 70 mm.

23. The device of claim 1 wherein the plurality of spaces formed between the plurality of wires range from about 1 $mm^2$ to about 400 $mm^2$.

24. A device comprising:
   48 round nitinol wires braided in a double overlapping pattern, wherein each of the wires has a diameter of about 0.28 mm and a length between about 10 cm and about 15 cm spanning between a proximal end of the device and a distal end of the device, wherein a braid density of the wires is about 7 ppi,
wherein the device is sufficiently designed to be positioned in at least a portion of an endoprosthesis implanted in a vessel,
wherein, when the device is in a relaxed state and positioned in the endoprosthesis, a plurality of spaces are formed between the plurality of wires to allow fluid to move freely through the plurality of spaces,
wherein, when the device is in a dilated state and positioned in the endoprosthesis, the plurality of wires are sufficiently designed to exert a radial force on the endoprosthesis while continually allowing the fluid to move freely through the plurality of spaces, and
wherein, when the device is in the dilated state and positioned in the endoprosthesis, the plurality of wires are sufficiently designed to conform to a diameter disparity ratio ranging from about 1:1 to about 10:1.

25. The device of claim 24 wherein, when the device is positioned in the endoprosthesis, the device is sufficiently designed to enhance primary attachment of the endoprosthesis to the single vessel.

26. The device of claim 24 wherein, when the device is positioned in the endoprosthesis, the device is sufficiently designed to repair a collapse in the endoprosthesis.

27. The device of claim 24 wherein, when the device is positioned in the endoprosthesis, the device is sufficiently designed to repair infolding of the endoprosthesis.

28. The device of claim 24 wherein, when the device is positioned in the endoprosthesis, the device is sufficiently designed to repair an endoleak in the endoprosthesis.

* * * * *